United States Patent
Das et al.

(10) Patent No.: US 8,951,539 B1
(45) Date of Patent: *Feb. 10, 2015

(54) METHODS OF PROMOTING ANGIOGENESIS USING CERIUM OXIDE NANOPARTICLES

(75) Inventors: Soumen Das, Orlando, FL (US); William Self, Orlando, FL (US); Sudipta Seal, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,891

(22) Filed: Jun. 7, 2012

Related U.S. Application Data

(60) Provisional application No. 61/493,994, filed on Jun. 7, 2011.

(51) Int. Cl.
- *A61K 33/24* (2006.01)
- *A61K 9/14* (2006.01)
- *A61P 9/00* (2006.01)
- *B82Y 5/00* (2011.01)
- *A61K 33/00* (2006.01)

(52) U.S. Cl.
CPC .............. *A61K 33/00* (2013.01); *Y10S 977/773* (2013.01); *Y10S 977/915* (2013.01); *Y10S 977/811* (2013.01)
USPC ........... 424/400; 424/617; 977/773; 977/915; 977/811

(58) Field of Classification Search
USPC ........................... 424/617; 977/773, 915, 811
See application file for complete search history.

(56) References Cited

U.S. PATENT DOCUMENTS

| | | | |
|---|---|---|---|
| 5,089,860 A | 2/1992 | Deppe et al. | |
| 5,411,647 A | 5/1995 | Johnson et al. | |
| 5,486,359 A | 1/1996 | Caplan et al. | |
| 5,910,311 A | 6/1999 | Boussouira | |
| 5,961,993 A | 10/1999 | Boussouira | |
| 6,042,714 A | 3/2000 | Lin et al. | |
| 6,103,247 A | 8/2000 | Boussouira | |
| 6,139,985 A | 10/2000 | Borglum et al. | |
| 6,316,012 B1 | 11/2001 | N'Guyen | |
| 6,327,074 B1 | 12/2001 | Bass et al. | |
| 6,368,577 B1 | 4/2002 | Kropf et al. | |
| 6,406,685 B1 | 6/2002 | Philippe | |
| 6,468,551 B1 | 10/2002 | Diec | |
| 6,497,863 B1 | 12/2002 | Wachter | |
| 6,497,865 B1 | 12/2002 | Griesbach | |
| 6,501,590 B2 | 12/2002 | Bass et al. | |
| 6,592,746 B1 | 7/2003 | Schmid-Schoenbein et al. | |
| 6,654,161 B2 | 11/2003 | Bass et al. | |
| 6,844,387 B2 | 1/2005 | Bass et al. | |
| 6,890,896 B1 | 5/2005 | Shashoua | |
| 7,005,504 B2 | 2/2006 | Hsei et al. | |
| 7,075,707 B1 | 7/2006 | Rapaport et al. | |
| 7,141,227 B2 | 11/2006 | Chan | |
| 7,270,813 B2 | 9/2007 | Shimp et al. | |
| 7,347,987 B2 | 3/2008 | McGinnis et al. | |
| 7,431,758 B2 | 10/2008 | Ota et al. | |
| 7,442,686 B2 | 10/2008 | Lasko et al. | |
| 7,471,706 B2 | 12/2008 | Bass et al. | |
| 7,504,356 B1 * | 3/2009 | Self et al. | ...................... 502/304 |
| 7,507,480 B2 | 3/2009 | Sugama | |
| 7,534,453 B1 | 5/2009 | Rzigalinski et al. | |
| 7,563,459 B2 | 7/2009 | Phillips et al. | |
| 7,642,250 B2 | 1/2010 | Williams | |
| 7,687,505 B2 | 3/2010 | Sugaya | |
| 7,725,802 B2 | 5/2010 | Eroz et al. | |
| 7,772,375 B2 | 8/2010 | Greferath et al. | |
| 7,888,119 B2 | 2/2011 | Sugaya et al. | |
| 7,899,093 B1 | 3/2011 | Bass et al. | |
| 7,906,147 B2 | 3/2011 | Hainfeld et al. | |
| 7,924,617 B2 | 4/2011 | Yip | |
| 8,080,420 B2 | 12/2011 | Sugaya | |
| 8,097,270 B2 | 1/2012 | Ketelson et al. | |
| 8,172,901 B2 | 5/2012 | Altman et al. | |
| 2003/0050709 A1 | 3/2003 | Noth et al. | |
| 2003/0187077 A1 | 10/2003 | Chane-Ching | |
| 2003/0228277 A1 | 12/2003 | Gehlsen | |
| 2004/0013658 A1 | 1/2004 | Fulton et al. | |
| 2004/0048808 A1 | 3/2004 | Hamdi et al. | |
| 2004/0062753 A1 | 4/2004 | Rezania et al. | |
| 2005/0159820 A1 | 7/2005 | Yoshikawa et al. | |
| 2005/0164377 A1 | 7/2005 | Miyabayashi et al. | |
| 2005/0171192 A1 | 8/2005 | Gehlsen | |
| 2006/0110440 A1 | 5/2006 | Sugaya et al. | |
| 2006/0134789 A1 | 6/2006 | Sugaya et al. | |
| 2006/0141137 A1 | 6/2006 | Anderson et al. | |
| 2006/0280729 A1 | 12/2006 | Mistry | |
| 2007/0003621 A1 | 1/2007 | Nangia et al. | |

(Continued)

FOREIGN PATENT DOCUMENTS

| WO | WO 99/15891 | 4/1999 |
|---|---|---|
| WO | WO 03/059263 A2 | 7/2003 |

(Continued)

OTHER PUBLICATIONS

Hyeon et al., Large-scale nonhydrolytic sol-gel synthesis of uniform-sized ceria nanocrystals with spherical, wire, and tadpole shapes, Angew. Chem. Int. Ed., 2005, vol. 44, pp. 7411-7414.*

(Continued)

*Primary Examiner* — Kortney L Klinkel
*Assistant Examiner* — Ping Cao
(74) *Attorney, Agent, or Firm* — Timothy H. Van Dyke; Beusse, Wolter, Sanks & Maire, P.A.

(57) ABSTRACT

Methods of using cerium oxide nanoparticles to promote angiogenesis are described. In a particular embodiment, a method of promoting angiogenesis in animal tissue comprises contacting the tissue with a composition comprising cerium oxide nanoparticles effective for stimulating proliferation of endothelial cells associated with the tissue.

9 Claims, 11 Drawing Sheets
(2 of 11 Drawing Sheet(s) Filed in Color)

(56) References Cited

U.S. PATENT DOCUMENTS

| | | | |
|---|---|---|---|
| 2007/0072825 | A1 | 3/2007 | Williams |
| 2007/0123996 | A1 | 5/2007 | Sugaya et al. |
| 2009/0087493 | A1 | 4/2009 | Dai et al. |
| 2009/0098574 | A1 | 4/2009 | Brisson et al. |
| 2009/0269410 | A1 | 10/2009 | McGinnis et al. |
| 2010/0098768 | A1 | 4/2010 | Andreescu et al. |
| 2010/0151000 | A1 | 6/2010 | Thomas et al. |
| 2010/0247428 | A1* | 9/2010 | Kim et al. ............ 424/1.11 |

FOREIGN PATENT DOCUMENTS

| | | | |
|---|---|---|---|
| WO | WO 2006/118954 A2 | 11/2006 | |
| WO | WO 2007/002662 A2 | 1/2007 | |
| WO | 2008064357 A2 | 5/2008 | |
| WO | WO 2008/064357 A2 | 5/2008 | |
| WO | WO2008064357 * | 5/2008 | ............ C12N 15/06 |
| WO | WO 2009/132277 A1 | 10/2009 | |

OTHER PUBLICATIONS

Ahluwalia et al., Critical role of hypoxia sensor -HIF1alpha in VEGF gene activation, implication for angiogenesis and tissue injury healing, Current Medicinal Chemistry, 2012, vol. 19, pp. 94.*

Park et al., oxidative stress induced by cerium oxide nanoparticles in cultured BEAS-2B cells, Toxicology, 2008, pp. 90-100.*

MSDS from Aldrich for cerium oxide powder bulk product.*

Riviere et al. penetration of intact skin by quantum dots with diverse physicochemical properties, Toxicological sciences, 2006, vol. 91, pp. 159-165.*

Seal et al., Size dependency variation in lattice parameter and valency states in nanocrystalline cerium oxides, Applied Physics Letters, 2005, vol. 87, pp. 133113-1-3.*

Baer et al., Ceria nanoparticles: planned and unplanned preparation and environmental impacts on particle properties. Sustainable Nanotechnology Organization, 2012, Arlington VA, pp. 1-26.*

A. B. Knott et al., "Nitric Oxide in Health and Disease of the Nervous System", Antioxid. Redox Signaling, 2009, vol. 11, pp. 541-554.

E. Isenovic et al., "Regulation of Endothelial Nitric Oxide Synthase in Pathophysiological Conditions", Cardiovasc. Hematol. Disord. Drug Targets, 2011, vol. 11, pp. 669-702.

M. C.Martinez et al. "Reactive Nitrogen Species: Molecular Mechanisms and Potential Significance in Health and Disease", Antioxid. Redox Signaling, 2009, vol. 11, pp. 669-702.

D. Pietraforte et al., "Peroxynitrite-dependent modifications of tyrosine residues in hemoglobin. Formation of tyrosyl radical(s) and 3-nitrotyrosine", Amino Acids, 2003, vol. 25, pp. 341-350.

T. Masui et al., "Preparation of ceria—zirconia sub-catalysts for automotive exhaust cleaning", J. Alloys Compd., 2000, vol. 303-304, pp. 49-55.

Y. Y. Tsai et al., "Reactive oxygen species scavenging properties of $ZrO_2$—$CeO_2$ solid solution nanoparticles", Nanomedicine, 2008, vol. 3, pp. 637-645.

R. M. Ferrizz et al., "Reaction of NO on $CeO_2$ and $Rh/CeO_2$ thin films supported on α-$A1_2O_3$(0001) and YSZ(100)", Surf. Sci., 2001, vol. 476, pp. 9-21.

M. Niwa et al., "Absorption of Nitric Oxide on Cerium Oxide", J. Colloid Interface Sci., 1982, vol. 86, pp. 260-265.

G. S. Qi et al, "$MnO_x$—$CeO_2$ mixed oxides prepared by co-precipitation for selective catalytic reduction of NO with $NH_3$ at low temperatures", Appl. Catal., B, 2004, vol. 51, pp. 93-106.

A. Martinez-Arias et al., :NO Reaction at Surface Oxygen Vacancies generated in Cerium Oxide, J. Chem. Soc., Faraday Trans., 1995, vol. 91, pp. 1679.

M. A. Sharpe et al., "Oxidation of nitric oxide by oxomanganese—salen complexes: a new mechanism for cellular protection by superoxide dismutase/catalase mimetics", Biochem. J., 2002, vol. 366, pp. 97-107.

M. E. Murphy et al., "Nitric Oxide Assay Using Hemoglobin Method",Methods Enzymol., 1994, vol. 233, pp. 240-250.

M. H. Lim et al., "Visualization of nitric oxide in living cells by a copper-based fluorescent probe", Nat. Chem. Biol., 2006, vol. 2, pp. 375-380.

S. Singh et al., "A phosphate-dependent shift in redox state of cerium oxide nanoparticles and its effects on catalytic properties", Biomaterials, 2011, vol. 32, pp. 6745-6753.

B. B. Wayland et al., "Spectroscopic Studies and Bonding Model for Nitric Oxide Complexes of Iron Porphyrins", J. Am. Chem. Soc., 1974, vol. 96, pp. 6037-6041.

M. R. Filipovic et al., "NO Dismutase Activity of Seven-Coordinate Manganese(II) Pentaazamacrocyclic Complexes", Angew. Chem., Int. Ed., 2008, vol. 47, pp. 8735-8739.

A. Y. Estevez et al., "Neuroprotective mechanisms of cerium oxide nanoparticles in a mouse hippocampal brain slice model of ischemia", Free Radical Biol. Med., 2011, vol. 51, pp. 1155-1163.

M.H. Lim et al., "Direct nitric oxide detection in aqueous solution by copper(II) fluorescein complexes", 2006, J Am Chem Soc vol. 128, pp. 14364-14373.

MJ Kampschreur et al, "Unraveling the source of nitric oxide emission during nitrification", 2007, Water Environ Res., vol. 79(13), pp. 2499-2509.

M. A. Ebrahimazadeh et al., "Nitric oxide radical scavenging potential of some Elburz medicinal plants", 2010, African J of Biotechnol., vol. 9(32), pp. 5212-5217.

G. Aliev et al., "Nitric Oxide as an initiator of brain lesions during the development of Alzheimer disease", 2009, Neurotox. Res., vol. 16, pp. 293-305.

L. Zhang et al., "Role of nitric oxide in Parkinson's disease", 2006, Pharmacol. Ther, vol. 109, pp. 33-41.

A.K. Nath et al, "The roles of nitric oxide in murine cardiovascular development", 2006, Dev. Biol, vol. 292, pp. 25-33.

F. Parkinson et al., "The role of nitric oxide in multiple sclerosis", Mar. 1997, J Mol Med (Berl), vol. 75(3), pp. 174-186.

J. Dowling et al., "Cerium oxide nanoparticles scavenge nitric oxide radical (•NO)", 2012, Chem. Commun, vol. 48, pp. 4896-4898.

F.J. Bonte et al., "Tc-99m HMPAO SPECT in the differential diagnosis of the dementias with histopathologic confirmation", Jul. 2006, Clin Nucl Med, vol. 31 (7), pp. 376-378.

N.J. Dougall et al, "Systematic review of the diagnostic accuracy of 99mTc-HMPAO-SPECT in dementia", 2004, Am J Geriatr Psychiatry, vol. 12 (6), pp. 554-570.

G. De Meyer et al., "Diagnosis-Independent Alzheimer Disease Biomarker Signature in Cognitively Normal Elderly People", Aug. 2010, Arch Neurol. vol. 67 (8), pp. 949-956.

A.S., Karakoti et al., ",Nanoceria as antioxidant: Synthesis and biomedical applications", 2008, JOM vol. 60, pp. 33-37.

R. Stuven et al, "Nitrification and Denitrification as a Source for NO and NO2 Production in High Strength Wastewater", 2001, Wat. Res. vol. 35, No. 8, pp. 1905-1914.

Hirst, Suzanne M. et al., "Anti-inflamamatory Properties of Cerium Oxide Nanoparticles", Small, 2009: vol. 5 pp. 2848-2856.

Kuchibhatla, S. et al., "Symmetry-Driven Spontaneous Self-Assembly of Nanoscale Ceria Building Blocks to Fractal Superoctahedra", Crystal Growth & Design, 2009; vol. 9(3) pp. 1614-1620.

Vlahakis, et al., "Integrin α9 β1 Directly Binds to Vascular Endothelial Growth Factor (VEGF)-A and Contributes to VEGF-A-induced Angiogenesis", Journal of Biological Chemistry, 2007, 282 vol. 20 pp. 15187-15196.

Fang, et al., "Matrix metalloproteinase-2 is required for the switch to the angiogenic phenotype in a tumor model", Proceedings of the National Academy of Sciences, 2000, vol. 97(8) pp. 3884-3889.

Varia, et al., "Pimonidazole: A Novel Hypoxia Marker for Complementary Study of Tumor Hypoxia and Cell Proliferation in Cervical Carcinoma", Gynecologic Oncology, 1998, vol (2) pp. 270-277.

Dong et al., "Activation of glassy carbon electrodes by dispersed metal oxide particles", J. Electrochem Soc., 1984, pp. 813-819.

de Wever, O., et al, "Role of tissue stroma in cancer cell invasion." J. Pathol. vol. 200, pp. 429-447 (2003).

Liotta, L. A. , et al, "The microenvironment of the tumour-host interface." Nature vol. 411, pp. 375-379 (2001).

Pupa, S. M. et al. "New insights into the role of extracellular matrix during tumor onset and progression." J. Cell. Physiol. vol. 192, pp. 259-267 (2002).

(56) References Cited

OTHER PUBLICATIONS

Cat, B, et al. "Enhancement of tumor invasion depends on transdifferentiation of skin fibroblasts mediated by reactive oxygen species." J. Cell Sci. vol. 119, pp. 2727-2738 (2006).

Kunz-Schughart, et al, "Tumor-associated fibroblasts (part II): functional impact on tumor tissue." Histol. Histopathol. vol. 17, pp. 623-637 (2002).

Desmouliere, A. et al. "The stroma reaction myofibroblast: a key player in the control of tumor cell behavior." Int. J. Dev. Biol. vol. 48: pp. 509-517 (2004).

Cerutti, P. et al. "The role of the cellular antioxidant defense in oxidant carcinogenesis." Environ. Health Perspect. vol. 102, pp. 123-129 (1994).

Freitas, R. A. "What is nanomedicine?" Nanomedicine vol. 1, pp. 2-9 (2005).

Barry, S. E. "Challenges in the development of magnetic particles for therapeutic applications." Int. J. Hyperth. vol. 24, pp. 451-466 (2008).

Corchero, J. L., et al "Biomedical applications of distally controlled magnetic nanoparticles." Trends Biotechnol. vol. 27, pp. 468-476 (2009).

Lin, W. et al. Toxicity of Cerium Oxide Nanoparticles in Human Lung Cancer Cells:, Int. J. of Toxicol., vol. 251 pp. 451-457 (2006).

Ristow, M. "Oxidative metabolism in cancer growth." Curr. Opin. Clin. Nutr. Metab. Care. vol. 9, pp. 339-345 (2006).

Karakoti, A. s. et al. "PEGylated Nanoceria as Radical Scavenger with Tunable Redox Chemistry." J. Am. Chem. Soc. vol. 131, pp. 14144-14145 (2009).

Thannickal, V. J., et al. "Reactive oxygen species in cell signaling." Am. J. Physiol. Lung Cell Mol. Physiol. vol. 279, pp. L1005-L1028 (2000).

Bayreuther K. et al. "Terminal differentiation, aging, apoptosis, and spontaneous transformation in fibroblast stem cell systems in vivo and in vitro." Ann. N. Y. Acad. Sci. vol. 663 1 pp. 167-179 (1992).

Boukamp, P. et al. "Phenotypic and genotypic characteristics of a cell line from a squamous cell carcinoma of human skin." J. Natl. Cancer Inst. vol. 68, pp. 415-427 (1982).

Stuhlmann, D. et al. "Modulation of homologous gap junctional intercellular communication of human dermal fibroblasts via a paracrine factors generated by squamous tumor cells." Carcinogenesis vol. 24, pp. 1737-1748 (2003).

Reynolds, E. S. "The use of lead citrate citrate at high pH as electron opaque stain in electron microscopy." J. Cell. Biol. vol. 17, pp. 208-212 (1963).

MocxSMAnn, T. "Rapid colorimetric growth and survival: application to assay for cellular proliferation and cytotoxicity assays. (1983)." J. Immunol. Methods vol. 65, pp. 55-63

Speckmann, B. et al. "Selenoprotein P expression is controlled through interaction of the coactivator PGC-1alpha with Fox01a and hepatocyte nuclear factor 4alpha transcription factors." Hepatology vol. 48, pp. 1998-2006 (2008).

Nishimura, M. et al. "Effects of prototypical drug•metabolizing enzyme inducers on mRNA expression of housekeeping genes in primary cultures of human and rat hepatocytes." Biochem. Biophys. Res. Commun. vol. pp. 346, 1033-1039 (2006).

Laemmli, "U K. Cleavage of structural proteins during the assembly of the head of bacteriophage T4." Nature vol. 227,.pp. 680-685 (1970).

Mauch, C. et al. "Regulation of collagen synthesis in fibroblasts within a three-dimensional collagen gel." Exp. Cell Res. vol. 178, pp. 493-503 (1988).

Damour, 0. et al. "A dermal substrate made of collagen-GAG-chitosan for deep burn coverage: first clinical uses." Clin. Mater. vol. 15, pp. 273-276 (1994).

Schlotmann, K. et al. "Cosmetic efficacy claims in vitro using a three-dimensional human skin model." Int. J. Cosmet. Sci. vol. 23, pp. 309-318 (2001).

Stuhlmann, D. et al. "Paracrine effect of TGF-beta1 on downregulation of gap junctional intercellular communication between human dermal fibroblasts." Biochem. Biophys. Res. Commun. vol. 319, pp. 321-326 (2004).

Heckert, E. G. et al. "Fenton-like reaction catalyzed by rare earth inner transition metal cerium." Environ. Sci. Technol. vol. 42, pp. 5014-5019 (2008).

Rzigalinski, B. A., et al. "Radical nanomedicine." Nanomedicine vol. 1, pp. 399-412 (2006).

Korsvik, C. et al. "Superoxide dismutase mimetic properties exhibited by vacancy engineered ceria nanoparticles." Chern. Commun. vol. 14, pp. 1056-1058 (2007).

Perez, J. M. et al. "Synthesis of biocompatible dextran-coated nanoceria with pH-dependent antioxidant properties." ASMAII vol. 4, pp. 552-556 (2008).

Auffan, M. et al. "Ce02 nanoparticles induce DNA damage towards human dermal fibroblasts in vi t:ro." Nanotoxicol. vol. 3, pp. 161-171 (2009).

Treiber, N. et al. "Overexpression of manganese superoxide dismutase in human dermal fibroblasts enhances the contraction of free floating collagen lattice: implications for ageing and hyperplastic scar formation." Arch. Dermatol. Res. vol. 301, pp. 273-287 (2009).

Kessler, D. et al. "Fibroblasts in mechanically stressed collagen lattices assume a "synthetic" phenotype." J. Biol. Chem. vol. 276, pp. 36575-36585 (2001).

Arora, P.D., et al. "Dependence of collagen remodelling on alpha-smooth muscle actin expression by fibroblasts." J. Cell. Physiol. vol. 159, pp. 161-175 (1994).

Ljinen, P. et al. "Transforming growth factor-beta 1 promotes contraction of collagen gel by cardiac fibroblasts through their differentiation into myofibroblats." Methods Find. Exp. Clin. Pharmacal. vol. 25, pp. 79-86 (2003).

Levine, R. L., et al. "Carbonyl assays for determination of oxidatively modified proteins." Methods Enzymol. vol. 233, pp. 346-357 (1994).

de Wever, et al, "Role of myofibroblasts at the invasion front." Biol. Chern. vol. 383, pp. 55-67 (2002).

Nadege, D. et al. "Mitochondria: from bioenergetics to the metabolic regulation of carcinogenesis." Front. Biosci. vol. 14, pp. 4015-4034 (2009).

Moller, P. et al. "Role of oxidative damage in toxicity of particulates." Free Radic. Res. vol. 44, pp. 1-46 (2010).

Oberdorster, G. et al. "Nanotoxicology: an emerging discipline evolving from studies of ultrafine particles." Environ. Health Perspect. vol. 113, pp. 823-829 (2005).

Shvedova, A. A. et al. "Exposure to carbon nanotube material: assessment of nanotube cytotoxicity using human keratinocyte cells." J. Toxicol. Environ. Health a vol. 66, pp. 1909-1926 (2003).

Warheit, D. B. "Nanoparticles: Health impacts? Mater." Today vol. 7, pp. 32-35 (2004).

Heckert, E. et al. "The role of cerium state in the SOD mimetic activity redox of nanoceria." Biomaterials vol. 29, pp. 2705-2709 (2008).

Harman D. "The Free Radical Theory of Aging." Antioxid Redox Sign 2003; vol. 5: pp. 557-561.

Halliwell B. "Oxidative stress and neurodegeneration: where are we now?" J Neurochem 2006; vol. 97: pp. 1634-1658.

Howes RM. "The Free Radical Fantasy." Ann New York Acad 2 o Scis, 2006; vol. 1067: pp. 22-26.

Warner OS, et al, "Oxidants, antioxidants and the ischemic brain." J Exp Bioi, 2004; vol. 207: pp. 3221-3231.

Inestrosa NC, et al. "Acetylcholinesterase Accelerates Assembly of Amyloid-[beta]-Peptides into Alzheimer's Fibrils: Possible Role of the Peripheral Site of the Enzyme Neuron" 1996; vol. 16: pp. 881-891.

Leker RR, et al. "Cerebral ischemia and trauma—different etiologies yet similar mechanisms: neuroprotective opportunities." Brain Research Reviews 2002; vol. 39: pp. 55-73.

Knott AB, et al. "Mitochondrial fragmentation in neurodegeneration." Nat Rev Neurosci 2008; vol. 9: pp. 505-518.

Korsvik C, et al. "Superoxide dismutase mimetic properties exhibited by vacancy engineered ceria nanoparticles." Chemi Commun, vol. 2007: pp. 1056-1058.

(56) References Cited

OTHER PUBLICATIONS

Santos MJ, et al. "Peroxisomal Proliferation Protects from -Amyloid Neurodegeneration." Journal of Biological Chemistry, 2005; vol. 280: pp. 41057-41068.

Aneggi E, et al. "Insights into the redox properties of ceria-based oxides and their implications in catalysis." J Alloys and Compounds 2006; vol. 408-412: pp. 1096-1102.

Naiki H, et al. "Kinetic analysis of amyloid fibril polymerization in vitro", Lab Invest, 1991; vol. 65: pp. 104-110.

Zhang F, et al. "Cerium oxidation state in ceria nanoparticles studied with X-ray photoelectron spectroscopy and absorption near edge spectroscopy." Surface Science, 2004; vol. 563: pp. 74-82.

Davis VT, et al. "Measurement of the Electron Affinity of Cerium." Phys Rev Lett, 2002; vol. 88.073003.

Karakoti A, et al. "Redox-active radical scavenging nanomaterials." Chern Soc Revs, 2010; vol. 39: pp. 4422-4432.

Varadarajan S, et al. "Different Mechanisms of Oxidative Stress and Neurotoxicity Alzheimer's a beta(1-42) andA beta(25-35)." Journal of the American Chemical Society, 2001; vol. 123: pp. 5625-5631.

White JA, et al. "Differential effects of oligomeric and fibrillar amyloid-[beta]1-42 on astrocyte-10 mediated inflammation." Neurobiology of Disease, 2005; vol. 18: pp. 459-465.

Celardo I, et al. "Cerium oxide nanoparticles: a promise for applications in therapy." J Exp Ther Oncol, 2011; vol. 9: pp. 47-51.

Celardo I, et al. "Pharmacological potential of cerium oxide nanoparticles." Nanoscale, 2011. [Epub ahead of print].

Hirst SM, et al. "Anti-inflammatory Properties of Cerium Oxide Nanoparticles." Small, 2009; vol. 5: pp. 2848-2856.

Alili L, et al. "Combined cytotoxic and anti-invasive properties of redox-active nanoparticles in tumor-stroma interactions." Biomaterials, 2011; vol. 32: pp. 2918-2929.

Colon J, et al. "Cerium oxide nanoparticles protect gastrointestinal epithelium from radiation-induced damage by reduction of reactive oxygen species and upregulation of superoxide dismutase 2." Nanomedicine-UK2010; vol. 6: pp. 698-705.

Varghese K, et al. "Regeneration and characterization of adult mouse hippocampal neurons in a defined in vitro system." J Neurosci Meth, 2009; vol. 177: pp. 51-59.

D'Angelo B, et al. "Falone Set ai..Cerium Oxide Nanoparticles Trigger Neuronal Survival in a Human Alzheimer Disease Model by Modulating BDNF Pathway." Curr Nanosci, 2009; vol. 5: pp. 167-176.

Vincent A, et al. "Protonated Nanoparticle Surface Governing Ligand Tethering and Cellular Targeting." ACS Nano 2009; vol. 3: pp. 1203-1211.

Di Loreto S, et al. "PPARagonists trigger neuronal differentiation in the human neuroblastoma cell line SH-SY5Y." J Cell Physiol 2007; vol. 211: pp. 837-847 (2007).

D'Angelo B, et al. "Signal transduction pathways involved in pparB/5-induced neuronal differentiation." J Cell Physiol, Epub ahead of print] (2010).

Cimini A. Benedetti E, et al. "Expression of peroxisome proliferator-activated receptors (PPARs) and retinoic acid receptors (RXRs) in rat cortical neurons." Neuroscience, 2005; vol. 130: pp. 325-337.

Teng HK, et al. "ProBDNF Induces Neuronal Apoptosis via Activation of a Receptor Complex of p75NTR and Sortilin." The Journal of Neuroscience, 2005; vol. 25:pp. 5455-5463.

Das M. et al. "Auto-catalytic ceria nanoparticles offer neuroprotection to adult rat spinal cord neurons." Biomaterials, 2007; vol. 28: pp. 1918-1925.

Munoz et al. "Neurotoxicity of acetylcholinesterase amyloid betapeptide aggregates is dependent on the type of Abeta peptide and the AChE concentration present in the complexes." FEBS Letters, 1999; vol. 450: pp. 205-209.

Karakoti AS, et al. "Thevuthasan S & SealS. PEGylated Inorganic Nanoparticles." Angewandte Chemie International Edition, 2011; vol. 50: pp. 1980-1994.

Hsu CH, et al. "Preparation and Characterization of Novel Coenzyme Q10 Nanoparticle Engineered from Microemulsion Precursors AAPS" PharmSciTech, 2003; vol. 4: pp. E32.

Cui Z et al. "Topical immunization using nanoengineered genetic vaccines." Journal of Controlled Release, 2002; vol. 81: pp. 173-184.

Cui Z, et al. "Genetic Immunization Using Nanoparticles Engineered from Microemulsion Precursors." Pharmaceutical Research, 2002; vol. 19: pp. 939-946.

Lockman PR, et al. "Assessment of Baseline Blood-Brain Barrier Parameters in the Presence of Novel Nanoparticles." Pharmaceutical Research, 2003; vol. 20: pp. 705-713.

Miranda S, et al. (2000) "The role of oxidative stress in the toxicity induced by amyloid [beta]-peptide in Alzheimer's disease." Progress in Neurobiology, vol. 62(6): pp. 633-648.

Kayed R, et al. (2003) "Common structure of soluble amyloid oligomers implies common mechanism of pathogenesis." (Translated from eng) Science, vol. 300(5618): pp. 486-489 (in eng).

Pietraforte D, et al, (2003) "Peroxynitrite-dependent modifications of tyrosine residues in hemoglobin. Formation of tyrosyl radical(s) and 3-nitrotyrosine." (Translated from eng) Amino Acids, vol. 25(3-4): pp. 341-350 (in eng).

Radi R, et al, (2001) "Unraveling peroxynitrite formation in biological systems." (Translated from eng) Free Radic Bid Med, vol. 30(5): pp. 463-488 (in eng).

Ye YZ, et al, (1996) "Antibodies that recognize nitrotyrosine." (Translated from eng) Methods Enzymol, vol. 269: pp. 201-209 (in eng).

Besancon E, et al, (2008) "Beyond NMDA and AMPA glutamate receptors: emerging mechanisms for ionic imbalance and cell death in stroke." (Translated from eng) Trends Pharmacol Sci, vol. 29(5): pp. 268-275 (in eng).

Smith DG, et al, (2007) "The redox chemistry of the Alzheimer's disease amyloid beta peptide." (Translated from eng) Biochim Biophys Acta, vol. 1768(8): pp. 1976-1990 (in eng).

Zhang YJ, et al, (2005) "Nitration and oligomerization of tau induced by peroxynitrite inhibit its microtubule-binding activity." (Translated from English) Febs Lett, vol. 579(11): pp. 2421-2427 (in English).

Crow JP, et al. (1997) "Superoxide dismutase catalyzes nitration of tyrosines by peroxynitrite in the rod and head domains of neurofilament-L." (Translated from eng) J Neurochem vol. 69(5): pp. 1945-1953 (in eng).

Tohgi H, et al. (1999) "Alterations of 3-nitrotyrosine concentration in the cerebrospinal fluid during aging and in patients with Alzheimer's disease." (Translated from eng) Neurosci Lett, vol. 269(1): pp. 52-54 (in eng).

Basso M, et al. (2009) "Characterization of Detergent-Insoluble Proteins in ALS Indicates a Causal Link between Nitrative Stress and Aggregation in Pathogenesis." PLoS One, vol. 4(12): pp. e8130.

Bishop A, et al. (2009) "Differential sensitivity of oligodendrocytes and motor neurons to reactive nitrogen species: implications for multiple sclerosis." (Translated from eng) J Neurochem, vol. 109(1): pp. 93-104 (in eng).

Ischiropoulos H & Beckman JS (2003) "Oxidative stress and nitration in neurodegeneration: cause, effect, or association?" (Translated from eng) J Clin Invest, vol. 111(2): pp. 163-169 (in eng).

Torreilles F, et al, (1999) "Neurodegenerative disorders: the role of peroxynitrite." (Translated from eng) Brain Res Brain Res Rev, vol. 30(2): pp. 153-163 (in eng).

Alkam T, et al. (2008) "The extensive nitration of neurofilament light chain in the hippocampus is associated with the cognitive impairment induced by amyloid beta in mice." (Translated from eng) J Pharmacol Exp Ther, vol. 327(1): pp. 137-147 (in eng).

Bonte FJ, et al, (Jul. 2006). "Tc-99m HMPAO SPECT in the differential diagnosis of the dementias with histopathologic confirmation". Clin Nucl Med, vol. 31 (7): pp. 376-378.

Dougall NJ, et al, (2004). "Systematic review of the diagnostic accuracy of 99mTc-HMPAO-SPECT in dementia". Am J Geriatr Psychiatry, vol. 12 (6): pp. 554-570.

De Meyer G, et al, (Aug. 2010). "Diagnosis-Independent Alzheimer Disease Biomarker Signature in Cognitively Normal Elderly People". Arch Neurol., vol. 67 (8): pp. 949-956. 111.

Martinez-Ruiz A, et al, "Nitric oxide signaling: classical, less classical, and nonclassical mechanisms." Free Radic Biol Med. vol. 2011; 51: pp. 17-29.

Stamler JS, et al, "Nitrosylation. the prototypic redox-based signaling mechanism." Cell. 2001; vol. 106(6): pp. 675-683.

(56) References Cited

OTHER PUBLICATIONS

Ghatan S. et al, "p38 MAP kinase mediates bax translocation in nitric oxide-induced apoptosis in neurons." J Cell Biol. 2000; vol. 150: pp. 335-347.
Knott AB, et al, "Mitochondrial fragmentation in neurodegeneration." Nat Rev Neurosci. 2008; vol. 9: pp. 505-518.
Manczak M, et al, "Impaired mitochondrial dynamics and abnormal interaction of amyloid of beta with mitochondrial protein Drp1 in neurons from patients with Alzheimer's disease: implications for neuronal damage." Hum Mol Genet. 2011; vol 20: pp. 2495-2509.
Ikiz B, et al, "A sequal to the tale of p25/Cdk5 in neurodegeneration." Neuron. 2008; vol 60: pp. 731-732.
Swerdlow RH. "Pathogenesis of Alzheimer's disease." Clin Interv Ageing. 2007; vol. 2: pp. 347-359.
Chaturvedi RK, et al, "Mitochondrial approaches for neuroprotection." Ann N Y Acad Sci. 2008; vol. 1147: pp. 395-412.
Estevez AY, et al. "Neuroprotective mechanisms of cerium oxide nanopartciles in a mouse hippocampal brain slice model of ischemia." Free Radic Biol Med. 2011; vol. 51: pp. 1155-1163.
Song W, et al. "Assessing mitochondrial morphology and dynamics using fluorescence wide-field microscopy and 3D image processing." Methods. 2008; vol. 46: pp. 295-303.
Bossy-Wetzel E, et al. "Crosstalk between nitric oxide and zinc pathways to neuronal cell death involving mitochondrial dysfunction and p38-activated K+ channels." Neuron. 2004; vol. 41: pp. 351-365.
Knott AB, et al "Impact of nitric oxide on metabolism in health and age-related disease." Diabetes Obes Metab. 2010; vol. 12: pp. 126-133.
Bossy,B, et al, "S-Nitrosylation of DRP1 does not affect enzymatc aactivity and is not specific to Alzheimer's disease." J Alzheimers Dis. 2010; vol. 20 Suppl 2: pp. S513-526.
Wang X, et al. "Impaired balance of mitochondrial fission and fusion in Alzheimer's disease." J Neurosci. 2009: vol. 29: pp. 9090-9103.
Taguchi N, et al "Mitotic phosphorylation of dynamin-related GTPase Drp1 participates in mitochondrial fission." J Biol Chem. 2007; vol. 282: pp. 11521-1152.
Yamano K, et al, "Coupling mitochondrial and cell division." Nat Cell Biol. 2011; vol. 13: pp. 1026-1027.
Nguyen MD, et al, "Cycling at the interface between neurodevelopment and neurodegeneration." Cell Death Differ. 2002; vol. 9: pp. 1294-1306.
Crews L, et al, "Molecular mechanisms of neurodegeneration in Alzheimer's disease." Hum Mol Genet. 2010; vol. 19: pp. R12-20.
Qu J, et al, "S-Nitrosylation activates Cdk5 and contributes to synaptic spine loss induced by beta-amyloid peptide." Proc Natl Acad Sci U S A. 2011; vol. 108: pp. 14330-14335.
Knott AB, et al, "Nitric oxide in health and disease of the nervous system." Antioxid Redox Signal. 2009; vol. 11: pp. 541-554.
Swerdlow RH, et al, "The Alzheimer's disease mitochondrial cascade hypothesis." J Alzheimers Dis. 2010; vol. 20 Suppl 2: pp. S265-279.
Chan DC. "Mitochondria: dynamic organelles in disease, aging, and development." Cell. 2006; vol. 125: pp. 1241-1252.
Drisko, J.A, et al., "The use of Antioxidants with First-Line Chemotherapy in Two Cases of Ovarian Cancer", J Am Coll Nut, 2003, vol. 22(2), pp. 118-123.
Korsvik et al., "Superoxide dismutase mimetic properties exhibited by vacancy engineered ceria nanoparticles", Chem. Commun., 2007, pp. 1056-1058.
Yu et al., "Large-scale nonhydrolytic sol-gel synthesis of uniform-sized ceria nanocrystals with spherical, wire, and tadpole shapes", Angew. Chem. Int. Ed., 2005, vol. 44, pp. 7411-7414.
Ahluwalia et al., "Critical role of hypoxia sensor -HIF1 alpha in VEGF gene activation, implication for angiogenesis and tissue injury healing", Current Medicinal Chemistry, 2012, vol. 19, p. 94.
Perez, J.M. et al., "Synthesis of Biocompatible Dextran-Coated Nanoceria with pH-Dependent Antioxidant Properties", 2008, Small, vol. 4, No. 5, pp. 552-556.
Griffiths, J.R., "Are Cancer Cells Acidic?", British Journal of Cancer, 1991, vol. 64, pp. 425-427.

De Wever, O. et al., "Stromal myofibroblasts are drivers of invasive cancer growth", International Journal of Cancer, 2008, vol. 123, pp. 2229-2238.
Lam, M.A., et al., "Nitric Oxide and Nitroxides Can Act as Efficient Scavengers of Protein-Derived Free Radicals", Chem Res. Toxicol, 2008, vol. 21, pp. 2111-2119.
Karakoti, A.S., et al., "Nanoceria as Antioxidant: Synthesis and Biomedical Applications", JOM, 2008, vol. 60(3), pp. 33-37.
Clinicaltrials.gov, "Clinical Trial for the Treatment of Diabetic Foot Ulcers Using a Nitric Oxide Releasing Patch: Pathon", (http://web.archive.org/web/20091130234819/http://clinicaltrials.gov/show/NCT/00428727) published online Nov. 30, 2009.
Deshpande et al., "Size dependency variation in lattice parameter and valency states in nanocrystalline cerium oxides", Appl;ied Physics Letters, 2005, vol. 87, pp. 133113-1-3.
Rasmussen et al., "Penetration of intact skin by quantum dots with diverse physiochemical properties", Toxicological Sciences, 2006, vol. 91, pp. 159-165.
Park et al., "Oxidative stress induced by cerium oxide nanoparticles in cultured BEAS-2B cells", Toxicology, 2008, vol. 245, pp. 90-100.
MSDA from Aldrich for cerium oxide powder bulk product, Feb. 2013, 6 pages.
Kuchibhatla, S. et al., "Hierarchicial assembly of inorganic nanostructure building blocks to octahedral superstructures—atrue template-free self-assembly", Nanotechnology, 2007, vol. 17 pp. 1-4.
Kuchibhatla, S, "Probing and Tuning the Size, Morphology, Chemistry and Structure of Nanoscale Cerium Oxide", Diss. University of Central Florida, 2008, 175 pp.
Giri, S et al., "Nanoceria: A Rare-Earth Nanoparticle as a Novel Anti-Angiogenic Therapeutic Agent in Ovarian Cancer", PLOS ONE, Jan. 2013, vol. 8, Issue 1, e54578.
Bast RC, Jr. et al, "Early detection of ovarian cancer: promise and reality", 2002, Cancer Treat Res vol. 107, pp. 61-97.
Friedlander, ML, "Prognostic factors in ovarian cancer", 1998, Semin Oneal, vol. 25, pp. 305-314.
Chen, J et al;, "Rare earth nanoparticles prevent retinal degeneration induced by intracellular peroxides", 2006, Nat Nanotechnol, vol. 1, pp. 142-150.
Das, M, et al, "Auto-catalytic ceria nanoparticles offer neuroprotection to adult rat spinal cord neurons", 2007, Biomaterials, vol. 28, pp. 1918-1925.
Tarnuzzer, RW et al., "Vacancy engineered ceria nanostructures for protection from radiation-induced cellular damage", 2005, Nano Lett vol. 5, pp. 2573-2577.
Patil, S et al, "Protein adsorption and cellular uptake of cerium oxide nanoparticles as a function of zeta potential", 2007, Biomaterials, vol. 28, pp. 4600-4607.
Carmeliet, P et al., "Angiogenesis in cancer and other diseases", 2000, Nature, vol. 407, pp. 249-257.
Kerbel, R et al., "Clinical translation of angiogenesis inhibitors", 2002, Nat Rev Cancer, vol. 2, pp. 727-739.
Ferrara, N, "Vascular endothelial growth factor", 1996, Eur J Cancer, vol. 32A, pp. 2413-2422.
Macchiarini, P. et al, "Relation of neovascularisation to metastasis of non-small-celllung cancer", 1992, Lancet, vol. 340, pp. 145-146.
Paley, PJ et al., "Vascular endothelial growth factor expression in early stage ovarian carcinoma", 1997, Cancer, vol. 80, pp. 98-106.
Weidner, N. et al, "Tumor angiogenesis correlates with metastasis in invasive prostate carcinoma", 1993, Am J Pathol, vol. 143, pp. 401-409.
Weidner, N et al., "Tumor angiogenesis and metastasis—correlation in invasive breast carcinoma", 1991, N Engl J Med, vol. 324, pp. 1-8.
Burger, RA et al., "Phase II trial of bevacizumab in persistent or recurrent epithelial ovarian cancer or primary peritoneal cancer: a Gynecologic Oncology Group Study", 2007, J Clin Oncol, vol. 25, pp. 5165-5171.
Narita, K et al, "HSulf-1 inhibits angiogenesis and tumorigenesis in vivo", 2006, Cancer Res, vol. 66, pp. 6025-6032.
Rattan, R et al., "Metformin attenuates ovarian cancer cell growth in an AMP-kinase dispensable manner", 2011, J Cell Mol Med. vol. 15, pp. 166-178.

(56) References Cited

OTHER PUBLICATIONS

Rattan, R et al., "5-Aminoimidazole-4-carboxamide-1-beta-D-ribofuranoside inhibits cancer cell proliferation in vitro and in vivo via AMP-activated protein kinase", 2005, J Bioi Chem, vol. 280, pp. 39582-39593.

Giri, S et al., "The role of AMPK in psychosine mediated effects on oligodendrocytes and astrocytes: implication for Krabbe disease", 2008, J Neurochem, vol. 105, pp. 1820-1833.

Giri, S et al., "Krabbe disease: psychosine-mediated activation of phospholipase A2 in oligodendrocyte cell death", 2006, J Lipid Res, vol. 47, pp. 1478-1492.

Malinda, Km et al., "Thymosin beta4 accelerates wound healing", 1999, J Invest Dermatol, vol. 113, pp. 364-368.

Rattan, R et al., "Metformin suppresses ovarian cancer growth and metastasis with enhancement of cisplatin cytotoxicity in vivo", 2011, Neoplasia in Press.

Chan, OW et al, "Loss of MKP3 mediated by oxidative stress enhances tumorigenicity and chemoresistance of ovarian cancer cells", 2008, Carcinogenesis, vol. 29, pp. 1742-1750.

Liu, LZ et al., "Reactive oxygen species regulate epidermal growth factor-induced vascular endothelial growth factor and hypoxia-inducible factor-1alpha expression through activation of AKT and P70S6K1 in human ovarian cancer cells", 2006, Free Radic Bioi Med, vol. 41, pp. 1521-1533.

Xia, C et al., "Reactive 1o oxygen species regulate angiogenesis and tumor growth through vascular endothelial growth factor", 2007, Cancer Res vol. 67, pp. 10823-10830.

Miyamoto, S et al., "New approach to cancer therapy: heparin binding-epidermal growth factor-like growth factor as a novel targeting molecule", 2007, Anticancer Res, vol. 27, pp. 3713-3721.

Gomez-Raposo, C et al., "Angiogenesis and ovarian cancer", 2009, Clin Transl Oncol, vol. 11, pp. 564-571.

Markman, M, "Antiangiogenic drugs in ovarian cancer", 2009, Expert Opin Pharmacother, vol. 10, pp. 2269-2277.

Lose, F et al., "Vascular endothelial growth factor gene polymorphisms and ovarian cancer survival", 2010, Gynecol Oneal, vol. 119, pp. 479-483.

Mesiano, S et al., "Role of vascular endothelial growth factor in ovarian cancer: inhibition of ascites formation by immunoneutralization", 1998, Am J Pathol, vol. 153, pp. 1249-1256.

Tempfer, C et al., "Vascular endothelial growth factor serum concentrations in ovarian cancer", 1998, Obstet Gynecol, vol. 92, pp. 360-363.

Xu, L et al., "Interleukin 8: an autocrine growth factor for human ovarian cancer", 2000, Oncol Res, vol. 12, pp. 97-106.

Takahashi, T et al., "A single autophosphorylation site on KDR/Fik-1 is essential for VEGF-A-dependent activation of PLC-gamma and DNA synthesis in vascular endothelial cells", 2001, Embo J, vol. 20, pp. 2768-2778.

Kroll, J et al., "The vascular endothelial growth factor receptor KDR activates multiple signal transduction pathways in porcine aortic endothelial cells", 1997, J Bioi Chern, vol. 272, pp. 32521-32527.

Bharali, OJ et al., "Emerging nanomedicines for early cancer detection and improved treatment: current perspective and future promise", 2010, Pharmacal Ther, vol. 128, pp. 324-335.

Seigneuric, R et al., "From nanotechnology to nanomedicine: applications to cancer research", 2010, Curr Mol Med, vol. 10, pp. 640-652.

Colon, J et al., "Protection from radiation-induced pneumonitis using cerium oxide nanoparticles", 2009, Nanomedicine, vol. 5, pp. 225-231.

Colon, J et al., "Cerium oxide nanoparticles protect gastrointestinal epithelium from radiation-induced damage by reduction of reactive oxygen species and upregulation of superoxide dismutase 2", 2010, Nanomedicine vol. 6, pp. 698-705.

Amin, KA et al., "The protective effects of cerium oxide nanoparticles against hepatic oxidative damage induced by monocrotaline", 2011, Int J Nanomedicine, vol. 6, pp. 143-149.

Alili, L et al., "Combined cytotoxic and anti-invasive properties of redox-active nanoparticles in tumor-stroma interactions", 2011, Biomaterials, vol. 32, pp. 2918-2929.

Hardas, SS et al., "Brain distribution and toxicological evaluation of a systemically delivered engineered nanoscale ceria", 2010, Toxicol Sci, vol. 116, pp. 562-576.

Folkman, J "Tumor angiogenesis: therapeutic implications:", 1971, N Engl J Med. vol. 285, pp. 1182-1186.

Cross, MJ et al., "VEGF receptor signal transduction", 2003, TRENDS in Biochem Sci, vol. 28, No. 9, pp. 488-494.

Ushio-Fukai M, et al., "Reactive oxygen species and angiogenesis: NADPH oxidase as target for cancer therapy", 2008, Cancer Lett, vol. 266, pp. 37-52.

Burger, RA, "Overview of anti-angiogenic agents in development for ovarian cancer", 2011, Gynecol Oncol, vol. 121, pp. 230-238.

Cannistra, SA et al., "Phase II study of bevacizumab in patients with platinum-resistant ovarian cancer or peritoneal serous cancer", 2007, J Clin Oncol, vol. 25, pp. 5180-5186.

Garcia, AA et al., "Phase II clinical trial of bevacizumab and low-dose metronomic oral cyclophosphamide in recurrent ovarian cancer: a trial of the California, Chicago, and Princess Margaret Hospital phase II consortia", 2008, J Clin Oncol, vol. 26, pp. 76-82.

o 4o Penson, RT et al., "Phase II study of carboplatin, paclitaxel, and bevacizumab with maintenance bevacizumab as first-line chemotherapy for advanced mullerian tumors", Jan. 2010, J Clin Oncol vol. 28, pp. 154-159.

Bansal, N et al., "Bladder perforation in a patient with recurrent epithelial ovarian cancer after treatment with bevacizumab", 2011, Gynecol Oncol, vol. 120, pp. 313-314.

Koskas, M et al., "Wound complications after bevacizumab treatment in patients operated on for ovarian cancer", 2010, Anticancer Res, vol. 30, pp. 4743-4747.

Seo YH, et al, "Profiling protein thiol oxidation in tumor cells using sulfenic acid-specific antibodies." Proceedings of the National Academy of Sciences of the United States of America vol. 106: pp. 16163-16168, 2009.

Sies H. "Strategies of Antioxidant Defense." European Journal of Biochemistry vol. 215: pp. 213-219, 1993.

Sies H, et al, Oxidative Stress—Damage to Intact-Cells and Organs. Philosophical Transactions of the Royal Society of London Series B-Biological Sciences vol. 311: pp. 617-631, 1985.

Stolk J, et al, "Characteristics of the inhibition of NADPH oxidase activation in neutrophils by apocynin, a methoxysubstituted catechol." Am J Respir Cell Mol Biol vol. 11: pp. 95-102, 1994.

Storz P. "Reactive oxygen species in tumor progression." Front Biosci vol. 10: pp. 1881-1896, 2005.

Stuhlmann D, et al, "Modulation of homologous gap junctional intercellular communication of human dermal fibroblasts via a paracrine factor(s) generated by squamous tumor cells." Carcinogenesis vol. 24: pp. 1737-1748, 2003.

Swietach P, et al, "Regulation of tumor pH and the role of carbonic anhydrase 9." Cancer Metastasis Rev vol. 26: pp. 299-310, 2007.

Tang Y, et al, "Caveolin-1 is related to invasion, survival, and poor prognosis in hepatocellular cancer," Med Oncol, vol. 29: pp. 977-984, 2012.

Thannickal VJ, et al, "Tyrosine phosphorylation regulates H2O2 production in lung fibroblasts stimulated by transforming growth factor beta 1." Journal of Biological Chemistry vol. 273: pp. 23611-23615, 1998.

Thannickal VJ, et al, "Reactive oxygen species in cell signaling." American Journal of Physiology-Lung Cellular and Molecular Physiology vol. 279: pp. L1005-L1028, 2000.

Thompson TC, et al, "The role of caveolin-1 in prostate cancer: clinical implications." Prostate Cancer Prostatic Dis vol. 13: pp. 6-11, 2010.

Tomayko MM, et al, "Determination of Subcutaneous Tumor Size in Athymic (Nude) Mice." Cancer Chemotherapy and Pharmacology vol. 24: pp. 148-154, 1989.

Valko M, et al, "Free radicals and antioxidants in normal physiological functions and human disease." Int J Biochem Cell Biol vol. 39: pp. 44-84, 2007.

Wittgen HG, et al. "Reactive oxygen species in melanoma and its therapeutic implications." Melanoma Res vol. 17: pp. 400-409, 2007.

(56) References Cited

OTHER PUBLICATIONS

Woiniak A, et al, "The effect of antitumor drugs on oxidative stress in B16 and S91 melanoma cells in vitro." Med Sci Monit vol. 11: pp. BR22-9, 2005.

Zhou M, et al, "A stable nonfluorescent derivative of resorufin for the fluorometric determination of trace hydrogen peroxide: applications in detecting the activity of phagocyte NADPH oxidase and other oxidases." Anal Biochem vol. 253: pp. 162-168, 1997.

Lecapentier, E et al., "Bevacizumab-induced small bowel perforation in a patient with breast cancer without intraabdominal metastases", 2010, Invest New Drugs, vol. 29, pp. 1500-1503.

Randall, LM et al, "Bevacizumab toxicities and their management in ovarian cancer", 2010, Gynecol Oncol, vol. 117, pp. 497-504.

Sokolov, et al.,"Real-time vital optical imaging of precancer using anti-epidermal growth factor receptor antibodies conjugated to gold nanoparticles." Cancer Res. 2003, vol. 63:1999, 2004.

Niu, J., et al. "Cardiovascular effects of cerium oxide nanoparticles in a transgenic murine model of cardiomyopathy," Cardiovas. Res. Nov. 30, 2006, Nov. 2006, vol. 73, No. 3, pp. 549-559.

Qureshi, M.A., et al. "Increased exhaled nitric oxide following autologous peripheral hemotopietic stem cell transplantation; a potential marker of idopathic pneumonia syndrome," Chest, Jan. 2004, vol. 125, No. 1, pp. 281-287.

Ohgushi, et al., "Stem Cell Technology and Bioceramics: From Cell to Gene Engineering", J. Biomed. Mat. Res. 48: 913-927; 1999.

Dal Maschio, et al., "Influence of Ce3+/Ce 4+ ratio on phase stability and residual stress field in ceria-yttria stabilized zirconia plasma-sprayed coatings", J. Mat. Sci. 27: 5591-5596; 1992.

Ramsfjell, et al., "Distinct Requirements for Optimal Growth and in Vitro Expansion of Human CD341CD382 Bone Marrow Long-Term Culture-Initiating Cells (LTC-IC), Extended LTC-IC, and Murine in Vivo Long-Term Reconstituting Stem Cells", Blood 99: 4093-4102; 1999.

Devasenpathi, et al., "Forming near net shape free-standing components by plasma spraying", Mat. Let. 57: 882-886; 2002.

Imamura, et al. "Drusen, choridal neovascularization and retinal pigment epithelium dysfunction in SOD1-deficient mice: A model of age-related macular degeneration," PNAS, vol. 103, No. 30; 11282-11287 (Jul. 25, 2006).

Hollyfield, et al. "Oxidative damage-induced inflammation initiates age-related macular degeneration," Nature Medicine, vol. 14, pp. 194-198 (2008).

Birch, et al. Age-related macular degeneration: a target for nanotechnology derived medicines. International Journal of Nanomedicine, 2007, 2(1), 65-77.

Maulik, N. Reactive oxygen species drives myocardial angiogenesis? Antioxidants & Redox Signaling, 2006, 8 (11-12) 2161-2168.

Kuchibhatla et al., "Hierarchical assembly of inorganic nanostructure building blocks to octahedral superstructures a true template-free self-assembly", Nanotechnology, 2007, vol. 18, pp. 1-4.

Ohia, et al. "Pharmacological consequences of oxidative stress in ocular tissues," Mutation Research, 2005, 579, 22-36.

Liu, et al. "Subtype lesions of neovascular age-related macular degeneration in Chinese paitents," Braefe's Arch Clin Exp Opthalmol, 2007, 245, 1441-1445.

Silva. "Seeing the benefits of ceria," Nature Nanotechnology, 2006, 1, 92-94.

Hahn, et al. "Maculas affected by Age-Related Macular Degeneration Contain Increased Chelatable Iron in the Retinal Pigment Epithelium and Bruch's Membrane," Arch. Opthalmol. 2003, 121, 1099-1105.

Haywood, et al. "Inflammation and Angiogenesis in Osteoarthritis," Arthritis & Rheumatism, 2003, 48 (8), 2173-2177.

Chen, et al. Rare Earth Nanoparticles Prevent Retinal Degeneration Induced By Intracellular Peroxides: Nature Nano Technology, 1(2) 142-148 (2006).

Moongkarndi, et al. "Antiproliferation, antioxidation and induction of apoptosis by Garcinia mangostana (mangosteen) on SKBR3 human breast cancer cell line," J. of Ethno-Pharmacology, vol. 90, (2004) pp. 161-166

Margrain, et al. "Do blue light filters confer protection against age-related macular degeneration?", Progress in Retinal and Eye Research, vol. 23 (2004) pp. 523-531

Bailey, et al. "Cerium Oxide Nanoparticles Extend Cell Longevity and Act as Free Radical Scavengers," online (retrieved on Apr. 24, 2006) from: http://www.med.miami.edu/mnbws/Rzigalinski11.html.

Tsai, Ming-Shyong. "The Study of the synthesis of nano-grade cerium oxide powder," Materials Letters 58, 2270-2274 (2004).

Rzigalinski, Beverly Ann, et al. "Cerium Oxide nanoparticles increase the lifespan of cultured brain cells and protect against free radical mechanical trauma" FASEB Journal, vol. 17 No. 4-5, Page Abstract No. 377.24 URL, XP008095016 & FASEB Meeting on Experimental Biology: Translating the Genome, San Diego, CA, USA, Apr. 11-15, 2003 Issn: 0892-6638.

Cook, et al. "Neuronal Damage induced by polychlorinated biphenyls is partically reversed by cerium oxide nanoparticles" [online] vol. 2003, 2003, XP008095032 Retrieved from the internet: URL http://sfn.scholarone.com/itin2003/main.htm]?new_page_id=126&abstract_id=14513&p_num=669.13&is_tech=0> [retrieved on Aug. 5, 2008].

Tusnekawa, S., et al. "Lattice relaxation of monosize Ce02-x nanocrystalline particles" Applied Surface Science Elsevier Netherlands, vol. 152, No. 1-2, Nov. 1999, pp. 53-56.

Hooper, Claire, Y., et al. "New treatment in age-related macular degeneration" Clinical & Experimental Opthalmology, Oct. 2003, pp. 376-391.

Qi, et al. "Redispersible Hybrid Nanopowders; Cerium Oxide Nanoparticle complexes with Phosphonated-PEG Oligomers," ACS Nano, 2008, vol. 2(5), pp. 879-888.

Otsuka, et al. "PEGylated nanoparticles for biological and pharmaceutical applications," Advanced Drug Delivery Reviews, 2003, vol. 55, pp. 403-419.

Olivier, et al. "Synthesis of pegylated immunonanoparticles." Pharmaceutical Research, Aug. 2002, vol. 19, No. 8, pp. 1137-1143.

Shui, Y.B., et al. "Morphological observation on cell death an dphagocytosis induced by ultraviolet irradiation in a culturated human lens epithelial cell line," Dec. 2000, vol. 71, pp. 609-618.

Xijuan, et al. "Size-dependent optical properties of nanocrystalline Ce02:Er obtained by combustion synthesis," Sep. 24, 2001, Phys. Chem. Chem Phys., vol. 3, pp. 5266-5269.

Guo, "Green and red upconversion luminescence in Ce02:Er3+ powders produced by 785 nm laser," Jounral of Solid State Chemistry 180, p. 127-131, 2007.

Perez, J. M., et al. "Synthesis of Biocompatible Dextran-Coated Nanoceria with pH-Dependent Antioxidant Properties," Small, vol. 4 No. 5, 2008, pp. 552-556.

Pirmohamed, et al. "Nanoceria exhibit redox state-dependent catalase mimetic activity," Chem. Comm, 2010, 46, pp. 2736-2738.

Nazem, et al. "Nanotechnology for Alzheimer's disease detection and treatment." Insciences J., 2011, vol. 1(4), pp. 169-193.

Karakoti, et al. "Direct Synthesis of Nanoceria in Aqueous Polyhydroxyl Solutions." J. Phys. Chem. C, vol. 111, No. 46, 2007, pp. 17232-17240.

Tarnuzzer, et al. "Vacancy Engineered Ceria Nanostructures for Protection from Radiation-Induced Cellular Damage," Nano Lett, vol. 4, No. 12, pp. 2573-2577.

Heckert, et al. "The role of cerium redox state in the SOD mimetic activity of nanoceria," Biomaterials, 29, 2008, pp. 2705-2709.

Schubert, et al. "Cerium and yttrium oxide nanoparticles are neuroprotective," Feb. 2006, Biochemical and Biophysical Research Communications, 342, p. 86-91.

Zhang, et al. Cerium oxide nanoparticles: size selective formation and structure analysis, Jan. 2002, Applied Physics Letters, vol. 81, No. 1, p. 127-129.

Patil, et al. "Surface-derived nanoceria with human carbonic anhydrase II inhibitors and flourphores: a potential drug delivery device." J. Phys. Chem. C., 2007, vol. 111, No. 24, pp. 8437-8442.

(56) References Cited

OTHER PUBLICATIONS

Patil, et al. "Synthesis of nanocrystalline ceria particles for high temperature oxidation resistant coating," Journal of Nanoparticle Research, 2002, vol. 4: pp. 433-438.

Jin, et al. "Nanopartical-mediated drug delivery and gene therapy," Biotechnol. Prog, 2007, vol. 23, pp. 32-41.

Eck, et al. "PEGylated gold nanoparticles conjugated to monoclonal F19 antibodies as targeted labeling agents for human pancreatic carcinoma tissue," ACS Nano, 2008, vol. 2(11) pp. 2263-2272.

NAFEE. Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwissenschaftilch-Technischen Fakul't III Chemie, Pharmazie, Bio-und Werstoffwissenschaften der Universit des Saarlandes, 2008.

Suh et al., "Multifunctional nanosystems at the interface of physical and life sciences", Nano Today, 2009, vol. 4, pp. 27-36.

Suzuki et al., "Preparation and characteristics of magnetite labelled antibody with the use of poly(ethylene glycol) derivatives", Biotechnol. Appl. Biochem., 1995, vol. 21, pp. 335-345.

Monte et al., "Inhibition of lymphocyte induced angiogenesis by free radical scavengers", Free Radic Biol Med, 1994, vol. 17, pp. 259-266.

PCT/US2011/0044329; PCT International Search Report and Written Opinion.

Ades EW, et al, HMEC-1: "establishment of an immortalized human microvascular endothelial cell line." J Invest Dermatol vol. 99: pp. 683-690, 1992.

Alili L, et al, "Suppression of tumor invasion by inorganic nanoparticles." Cancer Research vol. 69 pp (23 Suppl.): Boston, C42, 2009.

Alili L, at al, "Combined cytotoxic and anti-invasive properties of redox-active nanoparticles in tumor-stroma interactions." Biomaterials vol. 32: pp. 2918-2929, 2011.

Altekruse SF, et al, "SEER Cancer Statistics Review", 1975-2007. National Cancer Institute. Bethesda, MD, 2010.

Bardos JI, et al, "Negative and positive regulation of HIF-1: a complex network." Biochim Biophys Acta vol. 1755: pp. 107-120, 2005.

Bayreuther K, at al "Terminal differentiation, aging, apoptosis, and spontaneous transformation in fibroblast stem cell systems in vivo and in vitro," Ann N Y Acad Sci vol. 663: pp. 167-179, 1992.

Bhatia S, et al, "Treatment of metastatic melanoma: an overview." Oncology (Williston Park) vol. 23: pp. 488-496, 2009.

Boulares AH, et al, "Role of poly(ADP-ribose) polymerase (PARP) cleavage in apoptosis. Caspase 3-resistant PARP mutant increases rates of apoptosis in transfected cells." J Biol Chem vol. 274: pp. 22932-22940, 1999.

Brenneisen P, et al, "Central role of Ferrous/Ferric iron in the ultraviolet B irradiation-mediated signaling pathway leading to increased interstitial collagenase (matrix-degrading metalloprotease (MMP)-1) and stromelysin-1 (MMP-3) mRNA levels in cultured human dermal fibroblasts." J Biol Chem vol. 273: pp. 5279-5287, 1998.

Celardo I, et al, "Cerium oxide nanoparticles: a promise for applications in therapy." J Exp Ther Oncol vol. 9: pp. 47-51, 2011.

Deshpande S, et al, "Size dependency variation in lattice parameter and valency states in nanocrystalline cerium oxide." Appl. Phys. Lett. vol. 87, pp. 133113, 2005.

Deshpande S, et al, "Size dependency variation in lattice parameter and valency states in nanocrystalline cerium oxide." Appl. Phys. Lett. 87, pp. 133113, 2005.

De Wever O, et al, "Role of myofibroblasts at the invasion front." Biological Chemistry vol. 383: pp. 55-67, 2002.

Fang J, et al, "Tumor-targeted induction of oxystress for 14 cancer therapy." J Drug Target. vol. 15: pp. 475-486, 2007.

Freitas RA Jr. "What is nanomedicine?" Nanomedicine vol. 1: pp. 2-9, 2005.

Fruehauf JP, et al, "Reactive oxygen species: an Achilles' heel of 16 melanoma?" Expert Rev Anticancer Ther vol. 8: pp. 1751-1757, 2008.

Gao W, et al, "Effect of gold nanoparticles on glutathione depletion-induced hydrogen peroxide generation and apoptosis in HL7702 cells." Toxicol Lett vol. 205: pp. 86-95, 2011.

Garbe C, et al, "Melanoma epidemiology and trends." Clin Dermatol vol. 27: pp. 3-9, 2009.

Garbe C, et al, "Treatment of melanoma." Dtsch Arztebl Int vol. 105: pp. 845-851, 2008.

Giard DJ, et al, "In vitro cultivation of human tumors: establishment of cell lines derived from a series of solid tumors." J Natl Cancer Inst vol. 51: pp. 1417-1423, 1973.

Heckert EG, et al, "The role of cerium redox state in the SOD mimetic activity of nanoceria." Biomaterials vol. 29: pp. 2705-2709, 2008.

Helmlinger G, et al, "Interstitial pH and pO2 gradients in solid tumors in vivo: high-resolution measurements reveal a lack of correlation." Nat Med vol. 3: pp. 177-182, 1997.

Jahroudi N, et al, "The role of endothelial cells in tumor invasion and metastasis." J Neurooncol vol. 23: pp. 99-108, 1995.

Jemal A, et al, "Cancer statistics", 2008. CA Cancer J Clin vol. 58: pp. 71-96, 2008.

Kappus H, et al, "Toxic drug effects associated with oxygen metabolism: redox cycling and lipid peroxidation." Experientia vol. 37: pp. 1233-1241, 1981.

Karakoti AS, et al, "Direct synthesis of nanoceria in aqueous polyhydroxyl solutions." Journal of Physical Chemistry C vol. 111: pp. 17232-17240, 2007.

Karakoti AS, et al, "Nanoceria as Antioxidant: Synthesis and Biomedical Applications." Jom (1989) vol. 60: pp. 33-37, 2008.

Karakoti AS, et al, "Redox-active radical scavenging nanomaterials," Chem Soc Rev. vol. 39: pp. 4422-4432, 2010.

Kawiak A, et al, "Induction of Apoptosis in HL-60 Cells through the ROS-Mediated Mitochondrial Pathway by Ramentaceone from Drosera aliciae." Journal of Natural Products vol. 75: pp. 9-14, 2012.

ietzmann T, et al, "Reactive oxygen species in the control of hypoxia-inducible factor-mediated gene expression." Semin Cell Dev Biol vol. 16: pp. 474-486, 2005.

Korsvik C, et al, "Superoxide dismutase mimetic properties exhibited by vacancy engineered ceria nanopaticles." Chem Commun (Camb): 1056-1058, 2007.

Kuchibhatla S, et al, "One dimmensional nanostructed materials." Progress in Materials Science vol. 52: pp. 699-913, 2007.

Laemmli UK. Cleavage of structural proteins during the assembly of the head bacteriophage T4 Nature vol. 227: pp. 680-685, 1970.

Laurent A, et al, "Controlling tumor growth by modulating endogenous production of reactive oxygen species." Cancer Res vol. 65: pp. 948-956, 2005.

Levi F, et al, "High constant incidence rates of second primary neoplasms." Eur J Cancer Prev vol. 17: pp. 385-388, 2008.

Li P, et al, "Cytochrome c and dATP-dependent formation of Apaf-1/caspase-9 complex initiates an apoptotic protease cascade." Cell vol. 91: pp. 479-489, 1997.

Lin W, et al, "Toxicity of cerium oxide nanoparticles in human lung cancer cells." Int J Toxicol vol. 25: pp. 451-457, 2006.

Luanpitpong S, et al, "Regulation of lung cancer migration and invasion by reactive oxygen species and caveolin-1." J Biol Chem vol. 285: pp. 38832-38840, 2010.

Malecki JM, et al, "LY294002 and olomoucine synergize in promoting death of melanoma cells through activation of caspase-3 and apoptosis." Melanoma Res. vol. 20: pp. 52-58, 2010.

Mosmann T. "Rapid colorimetric assay for cellualr growth and surival: application to proliferation and cytotoxicity assays." J Immunol Methods vol. 65: pp. 55-63, 1993.

Nagata S. "Apoptosis by death factor." Cell vol. 88: pp. 355-365, 1997.

Nangaku M, et al, "A novel class of prolyl hydroxylase inhibitors induces angiogenesis and exerts organ protection against ischemia." Arterioscler Thromb Vasc Biol vol. 27: pp. 2548-2554, 2007.

Parums DV, et al, "JC70: a new monoclonal antibody that detects vascualr endothelium associated antigen on routinely processed tissue sections." J Clin Pathol vol. 43: pp. 752-757, 1990.

Pirmohamed T, et al, "Nanoceria exhibit redox state-dependent catalase mimetic activity." Chem. Commun. vol. 46: pp. 2736-273, 2010.

(56) References Cited

OTHER PUBLICATIONS

Quiles JL, et al, "Antioxidant nutrients and adriamycin toxicity," Toxicology vol. 180: pp. 79-95, 2002.

Reynolds ES. "Use of Lead Citrate at High Ph as an Electron-Opaque Stain in Electron Microscopy." Journal of Cell Biology vol. 17: pp. 208, 1963.

Roberts RA, et al, "Toxicological and pathophysiological roles of reactive oxygen and nitrogen species." Toxicology vol. 276: pp. 85-94, 2010.

Ruas JL, et al, "Hypoxia-dependent activation of HIF into a transcriptional regulator." Semin Cell Dev Biol vol. 16: pp. 514-522, 2005.

Sanchez Y, et al, "Regulation of genistein-induced differentiation in human acute myeloid leukaemia cells (HL60, NB4) Protein kinase modulation and reactive oxygen species generation." Biochemical Pharmacology vol. 77: pp. 384-396, 2009.

Saphir a. "Angiogenesis: the unifying concept in cancer?" J Natl Cancer Inst vol. 89: pp. 1658-1659, 1997.

Barrientos S, et al, (2008) "Growth factors and cytokines in wound healing." Wound Repair Regen. vol. 16: pp. 585-601 Chaloupka K, et al, (2010) "Nanosilver as a new generation of nanoproduct in biomedical applications." Trends Biotechnol. vol. 28: pp. 580-588.

Chen J, et al, (2006) "Rare earth nanoparticles prevent retinal degeneration induced by intracellular peroxides." Nat Nanotechnol. vol. 1: pp. 142-150.

Chigurupati S, et al, (2010) "A synthetic uric acid analog accelerates cutaneous wound healing in mice." PLoS One. 2010 vol Apr 6; pp. 5(4):e J0044.

Eming SA, et al, (2007) "Regulation of angiogenesis: wound healing as a model." Prog Histochem Cytochem. vol. 42: pp. 115-170.

Fadini GP, et al, (2010) "The redox enzyme p66Shc contributes to diabetes and ischemia-induced delay in cutaneous wound healing." Diabetes vol. 59: pp. 2306-2314.

Fitzmaurice SD, et al, (2011) "Antioxidant therapies for wound healing: a clinical guide to currently commercially available products." Skin Pharmacol Physiol. vol. 24: pp. 113-126.

Hirst SM, et al, (2009) "Anti-inflammatory properties of cerium oxide nanoparticles." Small vol. 5 :pp. 2848-2856.

Karakoti AS, et al, (2008) "Nanoceria as antioxidant: Synthesis and biomedical applications." JOM vol. 60: pp. 33-37.

Kong L, et al, (2011) "Nanoceria extend photoreceptor cell lifespan in tubby mice by modulation of apoptosis/survival signaling pathways." Neurobiol Dis. vol. 42: pp. 514-523.

Korsvik C, et al, (2007) "Superoxide dismutase mimetic properties exhibited by vacancy engineered ceria nanoparticles." Chem Commun (Camb). vol. 1: pp. 1056-1058.

Kyriazis GA, et al, (2008) "Numb endocytic adapter proteins regulate the transport and processing of the amyloid precursor protein in an isoform-dependent manner: implications for Alzheimer disease pathogenesis." J Biol Chem. vol. 283: pp. 25492-25502.

Lateef H, et al, (2005) "Pretreatment of diabetic rats with lipoic acid improves healing of subsequently-induced abrasion wounds." Arch Dermatol Res. vol. 297: pp. 75-83.

Mark RJ, et al, (1997) "Amyloid beta-peptide impairs glucose transport in hippocampal and cortical neurons: involvement of membrane lipid peroxidation." J Neurosci, vol. 17: pp. 1046-1054.

Martin P, et al, (2005) "Inflammatory cells during wound repair: the good, the bad and the ugly." Trends Cell Biol. vol. 15: pp. 599-607.

Menke NB, et al, (2007) "Impaired wound healing." Clin Dermatol. vol. 25: pp. 19-25,.

Mudge BP, et al, (2002) "Role of glutathione redox dysfunction in diabetic wounds." Wound Repair Regen. vol. 10: pp. 52-58.

Pedersen W A, et al, (1998) "Protein modification by the lipid peroxidation product 4-hydroxynonenal in the spinal cords of amyotrophic lateral sclerosis patients." Ann Neurol. vol. 44: pp. 819-824.

Pehr K, et al, (1993) "Why don't we use vitamin E in dermatology?" CMAJ vol. 149: pp. 1247-1253.

Rasik AM, et al, (2000) "Antioxidant status in delayed healing type of wounds." Int J Exp Pathol vol. 81: pp. 257-263.

Schafer M, et al, (2008) "Oxidative stress in normal and impaired wound repair." Pharmacol Res. vol. 58: pp. 165-171.

Sidhu GS, et al, (1998) "Enhancement of wound healing by curcumin in animals." Wound Repair Regen. vol. 6: pp. 167- 177.

Singh S, et al, (2010) "Unveiling the mechanism of uptake and sub-cellular distribution of cerium oxide nanoparticles." Mol Biosyst. vol. 6: pp. 1813-1820.

Waeg G, et al, (1996) "Monoclonal antibodies for detection of 4-ydroxynonenal modified proteins." Free Radic. Red. vol. 25: pp. 149-159.

Zhou Z, et al, CL (2010) "A novel class of compounds with cutaneous wound healing properties." J Biomed Nanotechnol. vol. 6: pp. 605-611.

Bossy-Wetzel E, et al, (2004) "Molecular pathways to neurodegeneration." Nat Med 10 Suppl:vol. 1 S, pp. 2-9.

Ferri CP, et al. (2005) "Global prevalence of dementia: a Delphi consensus study." Lancet, vol. 366(9503): pp. 2112-2117.

Markesbery WR (1997) "Oxidative stress hypothesis in Alzheimer's disease." Free Radic Biol Med, vol. 23(1): pp. 134-147.

Pacher P, et al, (2007) "Nitric oxide and peroxynitrite in health and disease." Physiol Rev, vol. 87 (1): pp. 315-424.

Barsoum MJ, et al, (2006) "Nitric oxide-induced mitochondrial fission is regulated by dynamin-related GTPases in neurons." EMBO J vol. 25(16): pp. 3900-3911.

Smith MA, et al, (1997) "Widespread peroxynitrite-mediated damage in Alzheimer's disease." J Neurosci, vol. 17(8): pp. 2653-2657.

Texel SJ & Mattson MP (2011) "Impaired adaptive cellular responses to oxidative stress and the pathogenesis of Alzheimer's disease." Antioxid Redox Signal, vol. 14(8): pp. 1519-1534.

Boczkowski J, et al, (2001) "Peroxynitrite-mediated mitochondrial dysfunction." Biol Signals Recept, vol. 10(1-2): pp. 66-80.

Shenker GM, et al. (2007) "Natural oligomers of the Alzheimer amyloid-beta protein induce reversible synapse loss by modulating an NMDA-type glutamate receptor-dependent signaling pathway." J Neurosci, vol. 27 (11): pp. 2866-2875.

Reynolds MR, et al. (2006) "Tau nitration occurs at tyrosine 29 in the fibrillar lesions of Alzheimer's disease and other tauopathies." J Neurosci, vol. 26(42): pp. 10636-10645.

Reyes JF, et al, (2008) "A possible link between astrocyte activation and tau nitration in Alzheimer's disease." Neurobiol Dis, vol. 31(2): pp. 198-208.

Cadenas E & Boveris A (2005) "Mitochondrial Free Radical Production, Antioxidant Defenses and Cell Signaling." Reactions, Processes, The Handbook of Environmental Chemistry, ed Grune T (Springer Berlin/Heidelberg), vol. 20, 615-643.

Mattson MP, (2008) "Mitochondria in neuroplasticity and neurological disorders." Neuron, vol. 60 (5): pp. 748-766.

Rabkin SW, et al, (2008) "Metalloporphyrins as a therapeutic drug class againt peoxynitrite in cardiovascular diseases involving ischemic reperfusion injury." Eur J Pharmacol, vol. 586: pp. (1-3):1-8.

Rong Y, et al, (1999) "EUK-134, a synthetic superoxide dismutase and catalase mimetic, prevents oxidative stress and attenuates kainate-induced neuropathology." Proc Natl Acad Sci U S A, vol. 96(17): pp. 9897-9902.

Sharpe MA, et al, (2002) "Oxidation of nitric oxide by oxomanganese-salen complexes: a new mechanism for cellular protection by superoxide dismutase/catalase mimetics." Biochem J, vol. 366(Pt 1): pp. 97-107.

van Empel VP, et al. (2006) "EUK-8, a superoxide dismutase and catalase mimetic, reduces cardiac oxidative stress and ameliorates pessure overoad-induced hear failure in the harequin mouse muant." J Am Coll Cardiol, vol. 48(4): pp. 824-832.

Celardo I, et al, (2011) "Phamacoogical potential of cerium oxide nanoparticles." Nanoscale, vol. 3(4): pp. 1411-1420.

Chen J, et al, (2006) "Rare earth nanoparticles prevent retinal degeneration induced by intracellular peroxides." Nat Nanotechnol, vol. 1(2): pp. 142-150.

Karakoti A, et al, (2010) "Redox-active radical scavenging nanomaterials." Chem Soc Rev, vol. 39(11): pp. 4422-4432.

Heckert EG, et al, (2008) "The role of cerium redox state in the SOD mimetic activity of nanoceria." Biomaterials, vol. 29(18): pp. 2705-2709.

(56) References Cited

OTHER PUBLICATIONS

Korsvik C, et al, (2007) "Superoxide dismutase mimetic properties exhibited by vacancy engineered ceria nanoparticles." Chem Commun, vol (10): pp. 1056-1058.

Pirmohamed T, et al. (2010) "Nanoceria exhibit redox state-dependent catalase mimetic activity." Chem Commun (Camb), vol. 46(16): pp. 2736-2738.

Anonymous (2009) "Cerium Oxide Nanoparticles Trigger Neuronal Survival in a Human Alzheimer Disease Model by Modulating BDNF Pathway." Current Nanoscience, vol. 5: pp. 167-176.

Das M, et al. (2007) "Auto-catalytic ceria nanoparticles offer neuroprotection to adult rat spinal cord neurons." Biomaterials, vol. 28(10): pp. 1918-1925.

Schubert D, et al, (2006) "Cerium and yttrium oxide nanoparticles are neuroprotective." Biochem Biophys Res Commun, vol. 342(1): pp. 86-91.

Hardas SS, et al. (2010) "Brain distribution and toxicological evaluation of a systemically delivered engineered nanoscale ceria." Toxicol Sci, vol. 116(2): pp. 562-576.

Hirst SM, et al. (2011) "Bio-distribution and in vivo antioxidant effects of cerium oxide nanoparticles in mice." Environ Toxicol.

Beckman JS (2009) "Understanding peroxynitrite biochemistry and its potential for treating human diseases." Arch Biochem Biophys, vol. 484(2): pp. 114-116.

Liot G, et al. (2009) "Complex II inhibition by 3-NP causes mitochondrial fragmentation and neuronal cell death via an NMDA- and ROS-dependent pathway." Cell Death Differ, vol. 16(6): pp. 899-909.

Viera L, et al, (1999) "Immunohistochemical methods to detect nitrotyrosine." Methods Enzymol, vol. 301: pp. 373-381.

Patil S, et al, (2002) "Synthesis of Nanocrystalline Ceria Particles for High Temperature Oxidation Resistant Coating." Journal of Nanoparticle Research, vol. 4(5): pp. 433-438.

Mailander V, et al, (2009) "Interaction of nanoparticles with cells." Biomacromolecules, vol. 10 (9): pp. 2379-2400.

Vincent A, et al. (2009) "Protonated nanoparticle surface governing ligand tethering and cellular targeting." ACS Nano, vol. 3(5): pp. 1203-1211.

Limbach LK, et al, (2005) "Oxide nanoparticle uptake in human lung fibroblasts: effects of particle size, agglomeration, and diffusion at low concentrations." Environ Sci Technol, vol. 39(23): pp. 9370-9376.

Owens DE, et al, (2006) "Opsonization, biodistribution, and pharmacokinetics of polymeric nanoparticles." Int J Pharm, vol. 307(1): pp. 93-102.

Radi R (1996) "Kinetic analysis of reactivity of peroxynitrite with biomolecules." Methods Enzymol, vol. 269: pp. 354-366.

Lymar SV, et al (1995) "Rapid reaction between peroxonitrite ion and carbon dioxide: Implications for biological activity." Journal of the American Chemical Society, vol. 117(34): pp. 8867-8868.

Pompella A, et al (2003) "The changing faces of glutathione, a cellular protagonist." Biochem Pharmacol, vol. 66(8): pp. 1499-1503.

Setsukinai K, et al (2003) "Development of novel fluorescence probes that can reliably detect reactive oxygen species and distinguish specific species." J Biol Chem, vol. 278(5): pp. 3170-3175.

Whiteman M & Halliwell B (1996) "Protection against peroxynitrite-dependent tyrosine nitration and alpha 1-antiproteinase inactivation by ascorbic acid. A comparison with other biological antioxidants." Free Radic Res, vol. 25(3): pp. 275-283.

Radi R, et al, (2002) "Nitric oxide and peroxynitrite interactions with mitochondria." Biol Chem, vol. 383(3-4): pp. 401-409.

Kumar A, et al, (2010) "Cell death mechanisms in the early stages of acute glutamate neurotoxicity." Neurosci Res, vol. 66(3): pp. 271-278.

Radi R, et al, (2002) "Peroxynitrite reactions and formation in mitochondria." Free Radic Biol Med, vol. 33(11): pp. 1451-1464.

Selkoe DJ (2004) "Cell biology of protein misfolding: the examples of Alzheimer's and Parkinson's diseases." Nat Cell Biol, vol. 6(11): pp. 1054-1061.

Kubo T, et al, (2002) "In vivo conversion of racemized beta-amyloid ([D-Ser 26]A beta 1-40) to truncated and toxic fragments ([D-Ser 26]A beta 25-35/40) and fragment presence in the brains of Alzheimer's patients." J Neurosci Res, vol. 70(3): pp. 474-483.

Esposito C, et al. (2006) "Exploring interaction of β-amyloid segment (25-35) with membrane models through paramagnetic probes." Journal of Peptide Science, vol. 12(12): pp. 766-774.

Millucci L, et al, (2009) "Rapid aggregation and assembly in aqueous solution of A beta (25-35) peptide." J Biosci, vol. 34(2): pp. 293-303.

Cho DH, et al. (2009) "S-nitrosylation of Drp1 mediates beta-amyloid-related mitochondrial fission and neuronal injury" Science, vol. 324(5923): pp. 102-105.

Glenner GG, et al (1984) "Alzheimer's disease: initial report of the purification and characterization of a novel cerebrovascular amyloid protein." Biochem Biophys Res Commun, vol. 120(3): pp. 885-890.

\* cited by examiner

HO1-heme oxygenase 1; TrxR-thioredoxin reductase

```
                        SEQUENCE LISTING

<160> NUMBER OF SEQ ID NOS: 8

<210> SEQ ID NO 1
<211> LENGTH: 26
<212> TYPE: DNA
<213> ORGANISM: Homo sapiens

<400> SEQUENCE: 1
ctgagttcat gaggaacttt cagaag                                           26

<210> SEQ ID NO 2
<211> LENGTH: 20
<212> TYPE: DNA
<213> ORGANISM: Homo sapiens

<400> SEQUENCE: 2
tggtacaggg aggccatcac                                                  20

<210> SEQ ID NO 3
<211> LENGTH: 20
<212> TYPE: DNA
<213> ORGANISM: Homo sapiens

<400> SEQUENCE: 3
gcagatcgag agcaagactg                                                  20

<210> SEQ ID NO 4
<211> LENGTH: 20
<212> TYPE: DNA
<213> ORGANISM: Homo sapiens

<400> SEQUENCE: 4
ctccagaaaa ttcacccacc                                                  20

<210> SEQ ID NO 5
<211> LENGTH: 24
<212> TYPE: DNA
<213> ORGANISM: Homo sapiens

<400> SEQUENCE: 5
acacattgtt ggaagaagca gccc                                             24

<210> SEQ ID NO 6
<211> LENGTH: 24
<212> TYPE: DNA
<213> ORGANISM: Homo sapiens

<400> SEQUENCE: 6
aggaaggtca accactcaca caca                                             24

<210> SEQ ID NO 7
<211> LENGTH: 21
<212> TYPE: DNA
<213> ORGANISM: Homo sapiens

<400> SEQUENCE: 7
agtagaggca gggatgatgt t                                                21
```

```
<210> SEQ ID NO 8
<211> LENGTH: 22
<212> TYPE: DNA
<213> ORGANISM: Homo sapiens

<400> SEQUENCE: 8
ctttggtatc gtggaaggac tc                                              22
```

METHODS OF PROMOTING ANGIOGENESIS USING CERIUM OXIDE NANOPARTICLES

CROSS-REFERENCE TO RELATED APPLICATION

Priority is claimed to provisional patent application Ser. No. 61/493,994 titled "Pro-angiogenic properties of cerium oxide nanoparticles: Role of surface $Ce^{3+}/Ce^{4+}$ ratio on induction of tube formation," which was filed Jun. 7, 2011 and is incorporated herein by reference in its entirety.

STATEMENT REGARDING FEDERALLY SPONSORED RESEARCH OR DEVELOPMENT

This invention was made with government support under grant 1R01AG031529-01 awarded by the National Institutes of Health and under grants 0708172 CBET and 080473355 CBET awarded by the National Science Foundation. The government has certain rights in the invention.

SEQUENCE LISTING

This application contains a Sequence Listing electronically submitted via EFS-web to the United States Patent and Trademark Office as a text file named "Sequence Listing.txt." The electronically filed Sequence Listing serves as both the paper copy required by 37 C.F.R. §1.821(c) and the computer readable file required by 37 C.F.R. §1.821(c). The information contained in the Sequence Listing is incorporated herein by reference in its entirety.

FIELD OF THE INVENTION

The invention relates to promoting angiogenesis and, more particularly, to using cerium oxide nanoparticles to promote angiogenesis.

BACKGROUND

Angiogenesis is an important physiological process in which new blood vessels form from pre-existing blood vessels. Compounds that target angiogenesis offer a route to treating diseases characterized by poor or abnormal vascularization of biological tissue. Abnormal angiogenesis can trigger pathological conditions such as cancer, chronic inflammation, diabetic retinopathy and arthritis. Insufficient angiogenesis is a major pathological component of chronic wounds or ischemic heart diseases.

Compounds aimed at treating diseases related to angiogenesis typically either inhibit or induce the creation of new blood vessels. Angiogenesis inhibitors are used to prevent new blood vessels from forming in areas where blood vessels should not form. In contrast, angiogenesis promoters are used in areas where the tissue requires new blood vessels to perform essential functions such as repairing wounds. Neo-vascularization should be promoted in such areas in order to transport nutrients to the site.

Angiogenesis can be promoted chemically by various endogenous angiogenic growth factors such as vascular endothelial growth factor ("VEGF") and fibroblast growth factor ("FGF"). VEGF-A and bFGF have been proposed to increase the blood flow to the damaged area. Cells called "endothelial cells" line mature blood vessels and typically do not proliferate. However, if endothelial cells are activated by an angiogenic growth factor, they will proliferate and migrate into un-vascularized tissue to form new blood vessels.

Blood vessels are surrounded by biological tissue in an extracellular matrix. The formation of new blood vessels is a function of the interactions between endothelial cells and the interaction of the endothelial cells with the extracellular matrix. These interactions are regulated by receptors on the surface of endothelial cells, which are sensitive to particular molecules such as angiogenic growth factors.

Angiogenesis can also be promoted chemically by applying non-endogenous compounds. For example, Eu(III) hydroxide nanorods are reported to have pro-angiogenic properties.

Cerium oxide nanoparticles exhibit interesting physical behavior, which has been exploited for various biological applications. Cerium oxide nanoparticles are typically considered to be antioxidants since they have been shown to scavenge reactive oxygen species or reactive oxygen intermediates. The antioxidant properties of cerium oxide nanoparticles are believed to be a function of the fact that, at the surface of the nanoparticles, cerium can be reversibly oxidized from a +3 state to a naturally stable +4 oxidation state.

Antioxidants typically inhibit, rather than promote, angiogenesis. Accordingly, the conventional wisdom on cerium oxide nanoparticles would suggest that they inhibit angiogenesis. Remarkably, the present inventors have unexpectedly found that cerium oxide nanoparticles also promote angiogenesis and are useful for treating physiological conditions that require the growth of new blood vessels in order to remediate the condition.

SUMMARY

In view of the foregoing, it is an object of the invention is to provide methods of promoting angiogenesis using cerium oxide nanoparticles.

In certain methods of the invention cerium oxide nanoparticles are used to promote angiogenesis in animal tissue. In such methods, angiogenesis is promoted in the tissue by contacting the tissue with a composition comprising cerium oxide nanoparticles effective for stimulating proliferation of endothelial cells associated with the tissue.

In certain methods of the invention cerium oxide nanoparticles are used to promote angiogenesis in a patient having a physiological condition that can be remediated by increasing endothelial cell proliferation by administering the cerium oxide nanoparticles to the patient.

In certain methods of the invention cerium oxide nanoparticles are used to promote angiogenesis in a patient having a condition that can be remediated by increasing endothelial cell proliferation by contacting the a tissue of the patient with cerium oxide nanoparticles in an amount sufficient to transiently lower the intracellular oxygen concentration of the tissue, wherein the transient lowering of the intracellular oxygen concentration stimulates expression of HIF1α, promotes proliferation of endothelial cells, and promotes angiogenesis in the tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Figure 1:
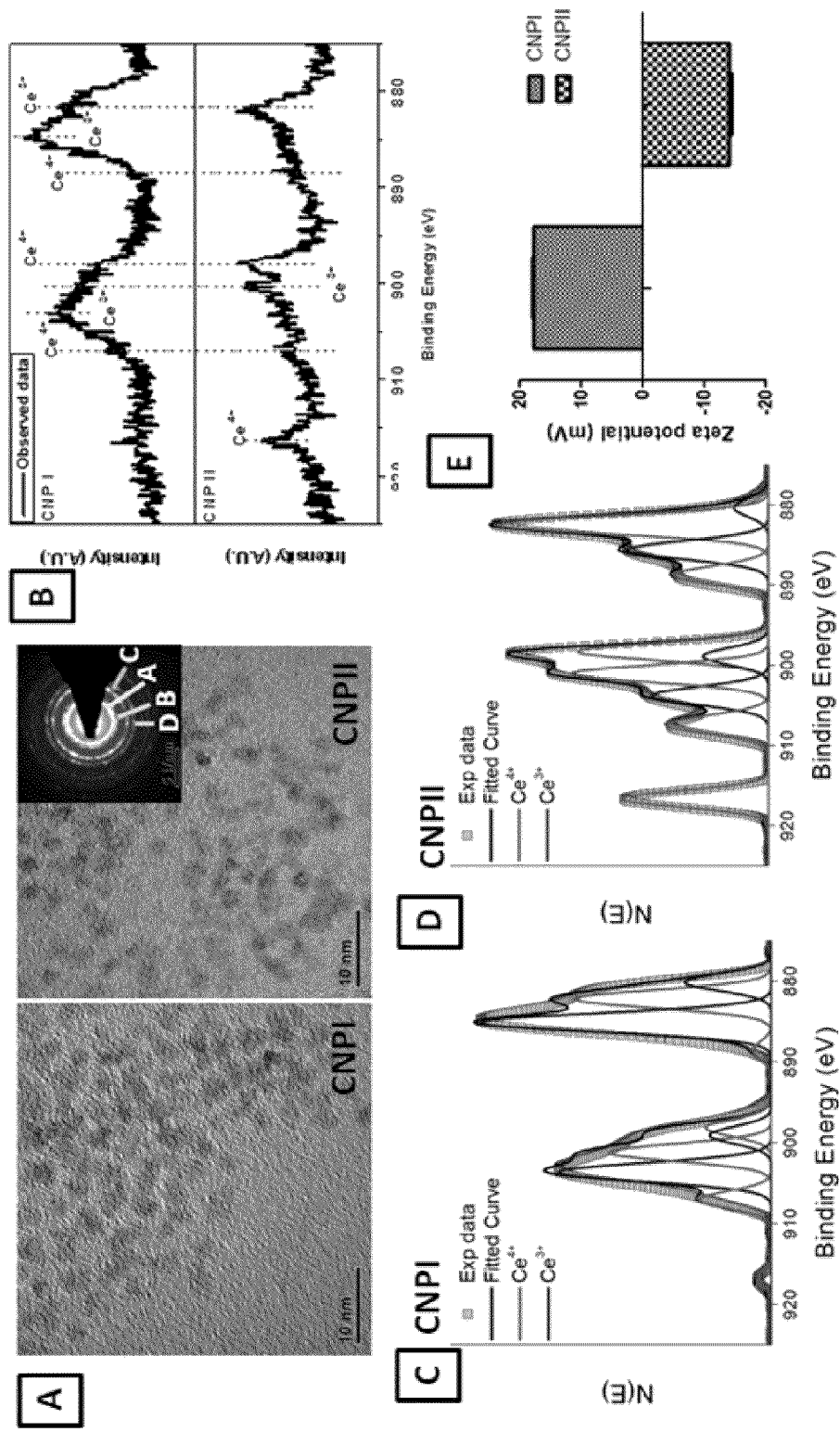
FIGS. 1A-D show the characterization of cerium oxide nanoparticles (CNPs). A shows HRTEM image of the differently synthesized CNPs (CNP-I & CNP-II), having similar shape and size (3-5 nm). The selected area electron diffraction (SAED) pattern in the inset of A confirms the fluorite structure where A (100), B (200), C (220), D (311) are the crystal plane of the lattice. B shows the XPS spectrum of CNP-I and CNP-II. C and D show deconvoluted XPS spectra of CNP-I and CNP-II. E shows the zeta potential of CNP-I and CNP-II.

In the Summary above and in the Detailed Description of Preferred Embodiments, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will be thorough and complete, and will convey the scope of the invention to those skilled in the art.

Embodiments of the invention involve the use of cerium oxide nanoparticles for promoting angiogenesis. A particular embodiment is a method of promoting angiogenesis in animal tissue. The method comprises contacting the tissue with a composition comprising cerium oxide nanoparticles effective for stimulating proliferation of endothelial cells associated with the tissue. Animal tissue includes but is not limited to living or artificial mammalian or non-mammalian tissue that is capable of being vascularized. The animal tissue is preferably a tissue for which neovascularization would provide a benefit, such as damaged tissue that needs neovascularization to heal, as opposed to a tissue in which neovascularization is to be avoided, such as certain cancerous tissues.

Contacting the tissue with the composition may be achieved by bringing or putting the composition into a state or condition of touching the tissue or being in immediate or local proximity to the tissue. Examples of techniques for contacting the tissue include conventional techniques for administering pharmaceutical substances such as, for example, intravenous, pericardial, oral, via implant, transmucosal, transdermal, intramuscular, subcutaneous, intraperitoneal, intrathecal, intralymphatical, intralesional, epidural, or topical administration techniques.

"Stimulating proliferation of endothelial cells" means that the cerium oxide nanoparticles are, at least in part, responsible for increasing the number of endothelial cells in the tissue. The increased number of endothelial cells allows for neovascularization of the tissue. Remarkably, the data discussed in the examples section show that cerium oxide nanoparticles can stimulate a 400% increase in angiogenesis when compared to a control sample.

Another particular embodiment of a method for promoting angiogenesis comprises administering cerium oxide nanoparticles to a patient having a physiological condition that can be remediated by increasing endothelial cell proliferation. The term "administering" means the giving or applying of a substance, including in vivo and/or ex vivo administration. Compositions may be administered systemically either orally, buccally, parenterally, topically, by inhalation or insufflations (i.e., through the mouth or through the nose), or rectally in dosage unit formulations containing conventional pharmaceutically acceptable carriers, adjuvants, and vehicles as desired, or may be locally administered by means such as, but not limited to, injection, implantation, grafting, topical application, or parenterally. Administering can be performed, for example, once, a plurality of times, and/or over one or more extended periods.

The term "physiological condition" means any abnormal physical or physiological condition characterized, at least in part, by a need for neovascularization in order to remediate the condition. Examples of such conditions include, but are not limited to: wounds and ischemic conditions where insufficient angiogenesis is the main cause of the pathology.

A "patient" is a human or other animal subject that has the physiological condition. Examples of patients include, but are not limited to mammalian subjects such as humans, mice, rats, dogs, pigs, rabbits, monkeys, or apes. Examples of patients also include, but are not limited to non-mammalian subjects such as chickens, for example.

Another particular embodiment of a method of promoting angiogenesis involves promoting angiogenesis in a patient having a condition that can be remediated by increasing proliferation of endothelial cells. In this embodiment, the method comprises contacting a tissue of the patient with cerium oxide nanoparticles in an amount sufficient to transiently lower an intracellular oxygen concentration of the tissue, wherein the transient lowering of the intracellular oxygen concentration stimulates expression of HIF1α and promotes proliferation of endothelial cells in the tissue.

In effect, contacting the tissue with the cerium oxide nanoparticles leads to a transient or short term decrease in the intracellular oxygen environment of the tissue. This, in turn, stimulates the expression of the angiogenic growth factor HIF1α, which promotes proliferation of endothelial cells and promotes angiogenesis.

Details about the cerium oxide nanoparticles and cerium oxide nanoparticles compositions useful in the methods of the invention are now described.

The cerium oxide nanoparticles may be mixed with other substances to provide a pharmaceutically acceptable dosage form. Examples of these substances include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, essential oils, emollients, dissolution enhancers, dispersing agents, or combinations thereof.

The cerium oxide nanoparticles may be spherical, rod-shaped, star-shaped, or polygonal. As discussed in the examples section, the shape of the cerium oxide nanoparticles apparently has little effect on their ability to promote angiogenesis with the exception being that the rod-shaped cerium oxide nanoparticles resulted in a slightly decreased endothelial cell proliferation.

In a preferred embodiment, the cerium oxide nanoparticles are spherically-shaped, meaning that they more or less approximate the shape of a sphere. Preferably, the average diameter of the spherically-shaped cerium oxide nanoparticles is about 15 nm or less, about 1 nm to about 15 nm, about 2 nm to about 6 nm, or about 3 nm to about 5 nm. In a particularly preferred embodiment, the spherically-shaped cerium oxide nanoparticles have an average diameter of 3 nm to 5 nm as measured by transmission electron microscopy. In embodiments in which the cerium oxide nanoparticles are not spherically shaped, it is preferred that the average dimension between two opposing sides of the nanoparticles is 15 nm or less.

The cerium oxide nanoparticles have a cerium oxide core with an external surface. The surface is characterized according to the percentage of Ce(3+) relative to Ce(4+) ions thereon. Although the amount is not intended to be limiting, when used in methods of the invention, some preferred ranges of Ce(3+):Ce(4+) percentages are: about 80%:20% to about 20%:80%, about 75%:25% to about 25%:75%, about 60%:40% to about 25%:75%, or about 57%:43% to about 27%:73%. In certain preferred embodiments, the percentage of Ce(3+) relative to Ce(4+) is >50% Ce(3+).

The concentration of cerium oxide in the composition that is administered to the patient or used to contact the tissue can be varied according to the type of administration or tissue being contacted. In preferred embodiments, the cerium oxide concentration in the composition is between about 0.5 µM to about 1.5 µM. In other preferred embodiments, the cerium oxide concentration in the composition is about 1 µM.

EXAMPLES

The following examples are provided for the purpose of illustration and do not limit the scope of the invention in any way.

Example 1

Preparation and Characterization of Cerium Oxide Nanoparticles

This example discusses the preparation and characterization of cerium oxide nanoparticles used in the subsequent examples.

Cerium oxide nanoparticles were prepared according to two different synthetic protocols. In either protocol 99.999% pure cerium nitrate hexahydrate purchased from Sigma Aldrich was used as a precursor reagent.

In the first synthetic protocol, the cerium oxide nanoparticles referred to herein as (CNP-I) were prepared using the wet chemical method described in an article titled "Anti-inflammatory Properties of Cerium Oxide Nanoparticles," published in Small 2009 5(24) at pages 2848-2856. The portion of this article that describes the synthesis of cerium oxide nanoparticles is incorporated herein by reference.

In the second synthetic protocol, the cerium oxide nanoparticles referred to herein as (CNP-II) were prepared using a conventional $NH_4OH$ precipitation method. Briefly, cerium nitrate hexahydrate was dissolved in deionized sterile water. A stoichiometric amount $NH_4OH$ was added to the cerium nitrate solution and was stirred for about 4 hr at room temperature. The cerium oxide nanoparticles that formed were subsequently separated from the solution by centrifugation at about 8000 g for about 10 minutes.

The size and morphology of the nanoparticles were analyzed using high resolution transmission electron microscopy (HRTEM), with a FEI Tecnai F30 having an energy dispersive X-ray (EDX) analyzer. The oxidation states of the cerium on the surface of the nanoparticle were calculated using a 5400 PHI ESCA (XPS) spectrometer and Mg—Kα X-radiation (1253.6 eV) at a power of 350 W.

As shown in FIG. 1A, the size of the CNP-I and CNP-II nanoparticles were typically about 3 to about 5 nm. For some experiments different sized nanoparticles were used, however. Cerium oxide nanoparticles having a size of about 10 nm to about 15 nm were purchased from from Alfa Aesar, Inc. Cerium oxide nanoparticles having a size of about 15 nm to about 20 nm were purchased from Nanostructure and Amorphous Inc. Cerium oxide nanoparticles having a size of about >25 nm were purchased from Sigma Aldrich, Inc. Cerium oxide nanoparticles having a size of about 50 nm to about 60 nm were purchased from Johnson Matthey, Plc.

One difference between CNP-I and CNP-II is that CNP-I and CNP-II include different ratios of $Ce^{3+}/Ce^{4+}$ on their surfaces. FIGS. 1B and C show the Ce (3d) XPS spectrum of CNP-I and CNP-II. CNP-I has a high $Ce^{3+}$ concentration (57%) as compared to CNP-II (27%). The $Ce^{3+}$ concentration was calculated as described in an article titled "Symmetry-Driven Spontaneous Self-Assembly of Nanoscale Ceria Building Blocks to Fractal Superoctahedra" published in *Crystal Growth & Design* 2009 9(3) at pages 1614-1620. The portion of that article describing how to calculate the concentration of cerium ions is incorporated by reference herein.

Another difference between CNP-I and CNP-II is that the surface charge of the nanoparticles has a different polarity. The surface charge is quantified using a parameter called a Zeta potential. The Zetapotentials of CNP-I and CNP-II are +17.78±O.5 and −14.05±O.83 mV, respectively, as shown in FIG. 1D.

Figure 2:
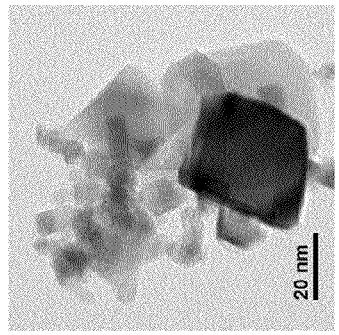
FIG. 2 shows representative HRTEM images of the different shaped and sized CNPs discussed in the examples section.
Figure 2:
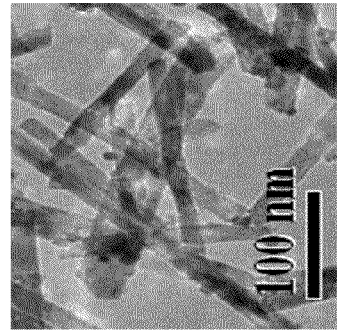
Figure 2:
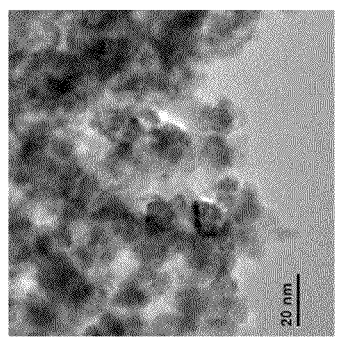
Figure 2:
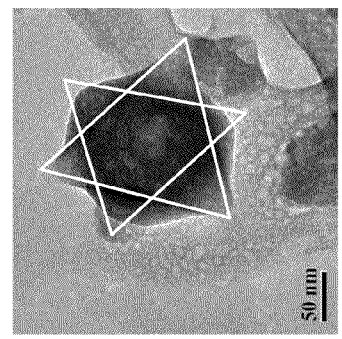
Figure 2:
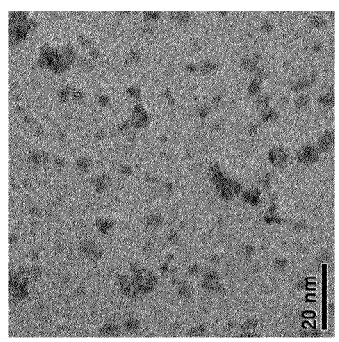
Figure 2:
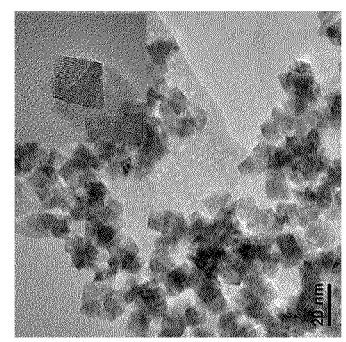
Figure 2:
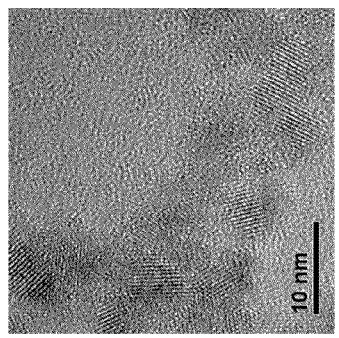
Figure 2:
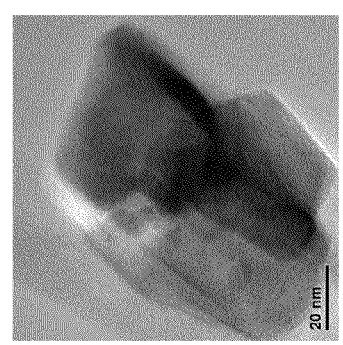

Cerium oxide nanoparticles with different shapes including stars, polygons, and nanorods have also been synthesized and confirmed by HRTEM (FIG. 2).

In the following examples, the cerium oxide nanoparticles samples were diluted in either phosphate buffer, saline solution, or cell culture media to the concentration indicated.

Example 2

CNP-I and CNP-II Induce the Formation of Endothelial Tubes

This example shows that cerium oxide nanoparticles promote proliferation of endothelial cells.

Figure 3:
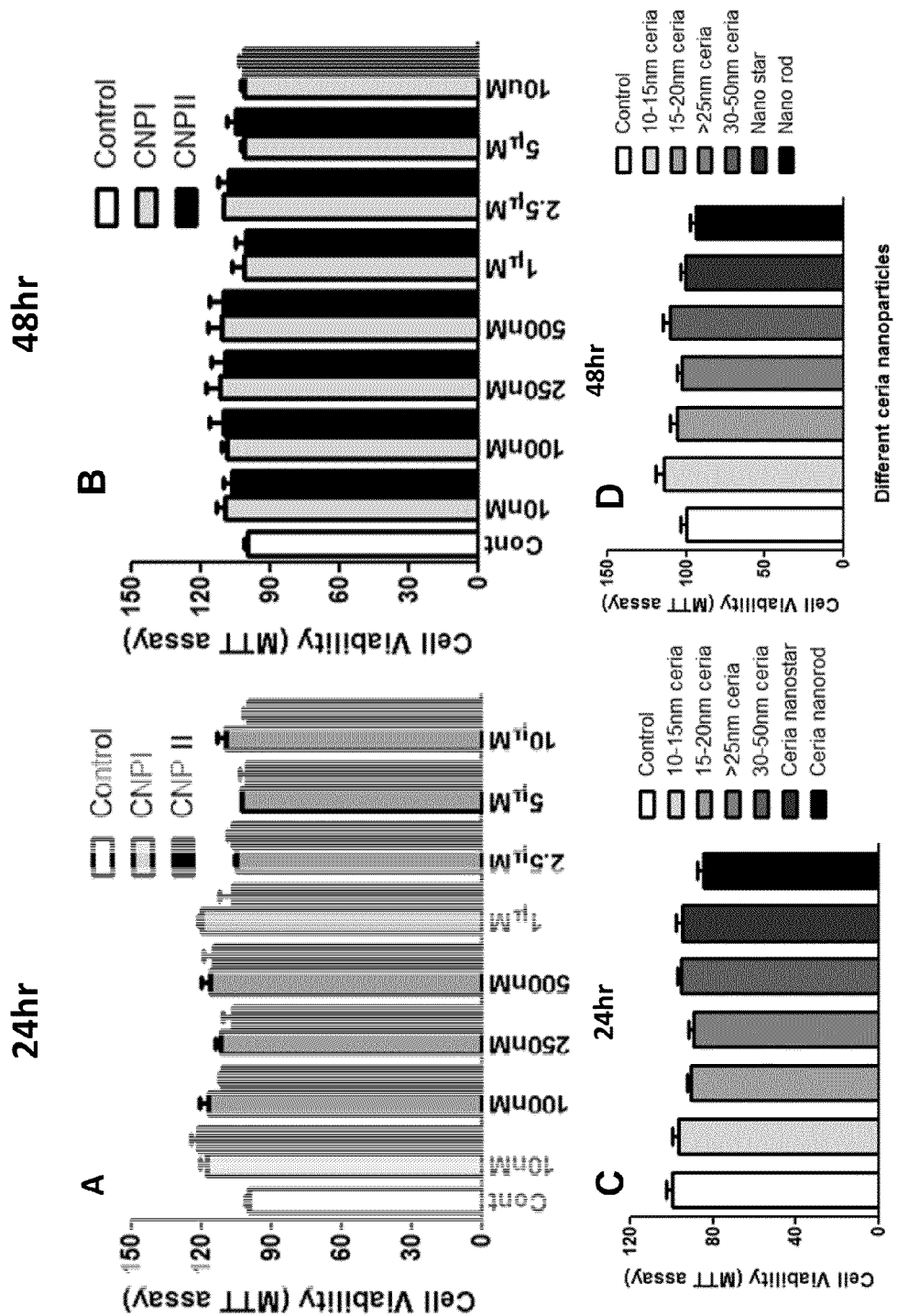
FIGS. 3A-D show the assessment of cell viability in HUVECs exposed to CNPs. HUVEC cells were cultured in endothelial cell media (ScienceCell, San Diego, Calif., USA) supplemented with 5% FBS and 100 IU ml−1 penicillin, and MTT dye reduction was assessed after 24 h (A) and 48 (B) treatment with varying concentrations of CNP-I and CNP-II. C and D are graphs that show the cell viability of cells treated with different size (10-15 nm), 15-20 nm, >25 nm and 30-50 nm) and shaped (star-shaped and rod-shaped) CNPs at 1000 nM concentration after 24 hr and 48 hr of incubation, respectively. The data are reported as the mean of multiple independent cultures and the error represents standard deviation.

Proliferation of endothelial cells is the first step involved in angiogenesis. Proliferation of the human umbilical vein endothelial cells (HUVECs) was estimated using the tetrazolium dye reduction (MTT) assay. No cytotoxicity was observed in cells exposed to either of the CNPs (FIGS. 3A and B). Cell proliferation was also analyzed in the presence of different size and shaped cerium oxide nanoparticles at a concentration of 1 µM (FIGS. 3C and D). With the exception of cerium oxide nanorods, other size and shaped nanoparticles did not reveal any overt toxicity towards HUVEC cells. Exposure to cerium oxide nanorods led to a slight reduction in cell proliferation (P>0.05).

Figure 4:
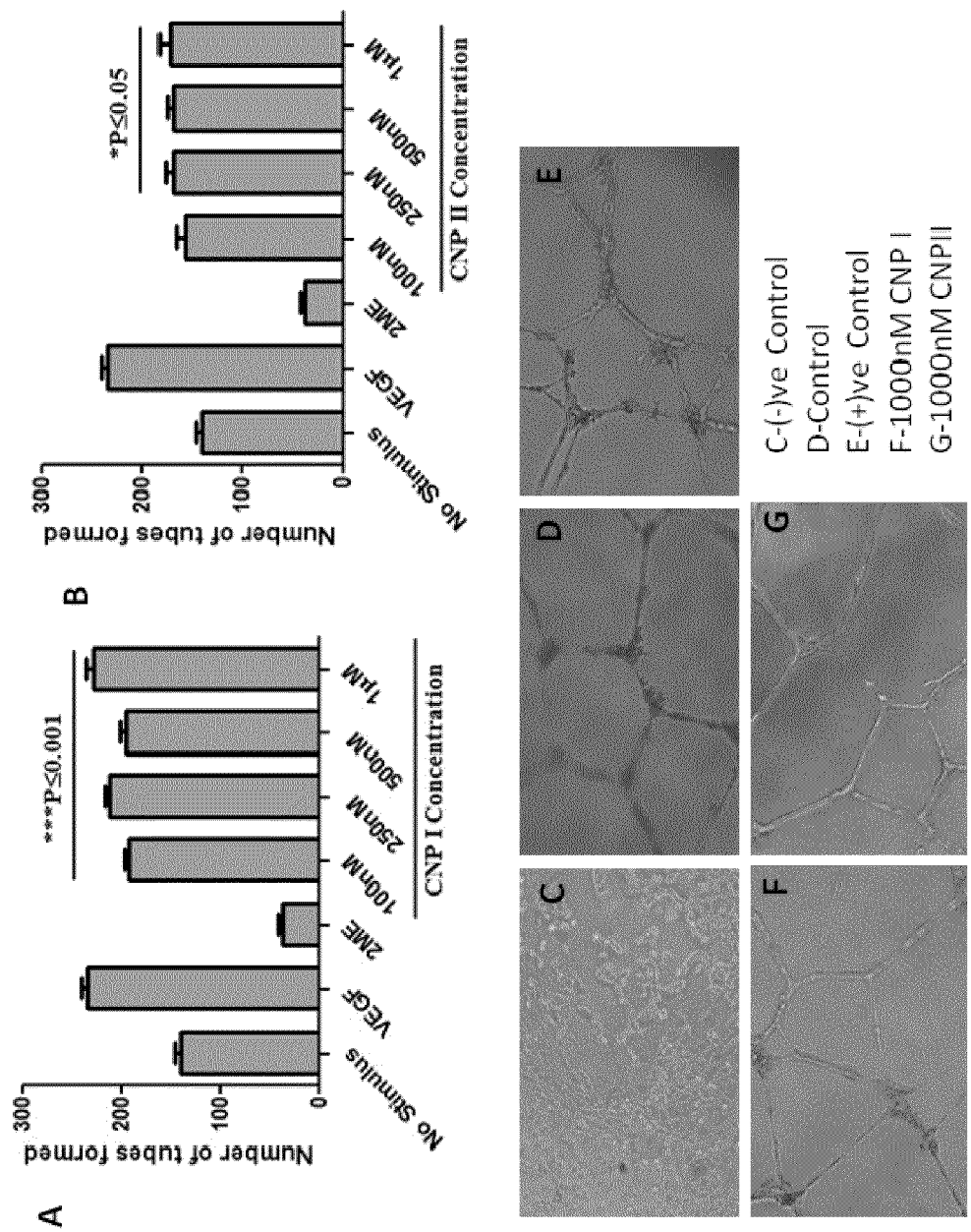
FIGS. 4A-G show that CNPs promote angiogenesis in HUVEC cell culture models. HUVEC cells were cultured with vehicle (control), 10 μM β-estradiol (negative control), 30 ng rVEGF (positive control) and varying concentrations of cerium oxide nanoparticles (100 nM to 1 μM CNP-I or CNP-II) and tube formation counted as the number of branches at 10× magnification after 8 hr of treatment. The data represent the mean of at least six different experiments and the plotted error represents the standard deviation. A and B show the number of tubes formed when cells were exposed to different concentrations of CNP-I and CNP-II respectively. Images of tubes formed in beta-estradiol (C), control (D), VEGF treated (E), 1 μM CNP-I treated (F) and 1000 nM CNP-II treated (G) after 8 hr of incubation are shown.

The endothelial tube formation assay is an in vitro model system where anti and pro-angiogenic molecules can be tested. FIG. 4 (A) shows the representative tube formation of the control, positive control (30 ng VEGF), negative control (10 pM 2-methoxyestradiol) and different concentrations of CNP-I exposure. Interestingly, we observed that the addition of CNP-I to cells resulted in a significant, concentration dependent, (P: −S; O.OOI; induction 40% of tube increase) formation. Further, up to 1 pM concentration increases of CNP-I up to 10 pM did not increase tube formation significantly (data not shown). A weaker induction of tube formation was seen (P: −S; O. 05; increase) with the addition of CNP-II (FIG. 4B.).

Figure 5:
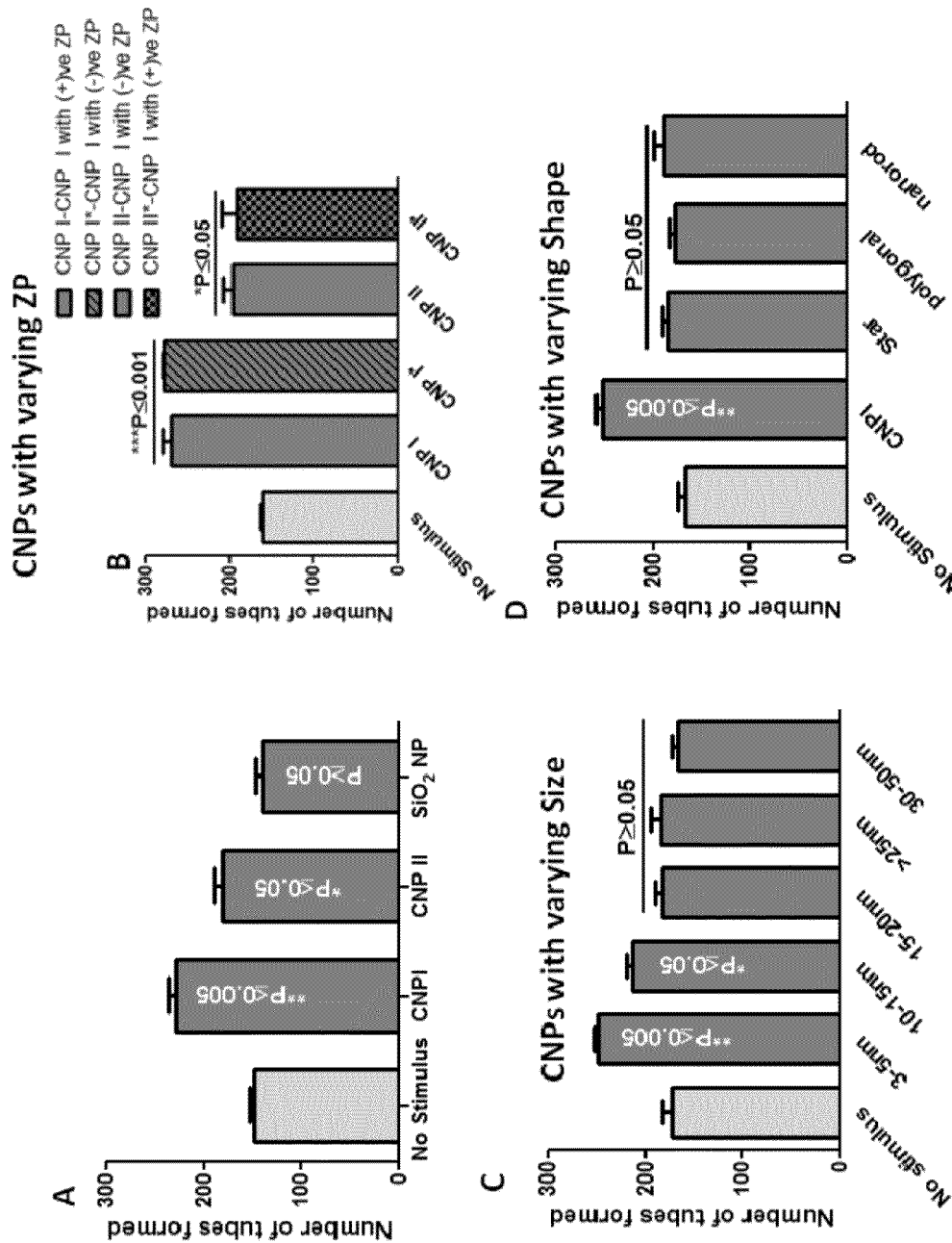
FIGS. 5A-D shows the effect of the $Ce^{3+}/Ce^{4+}$ ratio, zeta potential, size and shape of CNPs on tube formation. Tube formation in (A) CNP-I ($Ce^{3+}/Ce^{4+}\rightarrow 1.33$), CNP-II ($Ce^{3+}/Ce^{4+}\rightarrow 0.37$) and $SiO_2$; (B) CNP with different zeta potentials: CNP-I (+17.78±0.5 mV), CNP-I' (−20±1.4 mV), CNP-II (−14.05±0.83 mV) and CNP-II' (+34.05±0.52 mV); (C) CNPs with varying size; (D) CNPs with varying shape. All the experiments were carried out with cells exposed to nanoparticles at a concentration of 1 μM. The data represent a mean of at least six experiments and the error plotted represents the standard deviation.

To confirm that tube formation induction is a unique property of CNPs, a similar sized $SiO_2$ nanoparticle (5-10 nm; FIG. 2) was tested and no tubes were observed (FIG. 5A). We also determined Lipopolysaccharide (LPS) contamination, because low levels of LPS may influence the tube formation assay. LPS was not detected using either of the CNPs (<0.005 EU/ml), showing that induction of tube formation is an intrinsic property of CNPs.

To determine whether the promotion of endothelial tube formation is a function of surface charge, we tested the effect of tube formation using CNP-I and CNP-II with inverted surface charge by treating the CNP-I and CNP-II with acid (1 mM HCL) or base (1 mM NaOH) while stirring for about 4 to about 6 hrs. After thorough washing with $dH_2O$, the inverted zeta potential of CNP-I* and CNP-II* was altered to −20±1.4 mV and +44.08±1.1 mV, respectively. We did not notice a difference between the promotion of tube formation when cells were treated with the original CNPs or the CNPs with inverted zeta potentials (FIG. 5B).

We also determined whether the endothelial cell culture medium (ECM) influenced the surface charge of CNP-I and CNP-II. CNP-I and CNP-II were analyzed after 1 hr incubation in ECM in the absence of cells. Both types of nanoparticles showed a net negative surface charge of about −9.23±0.56 mV. This suggests that CNPs interact with components of ECM, thereby shifting the surface charge towards the negative. Our combined results indicate that surface charge does not influence tube induction.

To determine possible size and shape effects, CNPs spanning: 3-5, 10-15, 15-20, >25 and 50-60 nm were exposed to HUVECS at a concentration of 1 µM. As shown in FIG. 5C, the 3-5 nm and 10-15 nm sized CNPs showed induced tube formation while exposing HUVECS to CNPs >15 nm in size did not result in tube formation. The micron size particles inhibited tube formation, though the inhibition was not statistically significant.

The size modulation may be linked to a change in the mechanism by which the cells interact with the CNPs. To eliminate this possibility, HUVECs were exposed to different shaped CNPs all having a size >15 nm. No discernible difference in tube formation was observed as a function of shape (FIG. 5D).

Example 3

CNP-I and CNP-II Promote Mature Vascular Sprouting in Chick Chorioallantoic Membrane (CAM) Sprouting Assay This examples shows that cerium oxide nanoparticles promote vascular sprouting.

Figure 6:
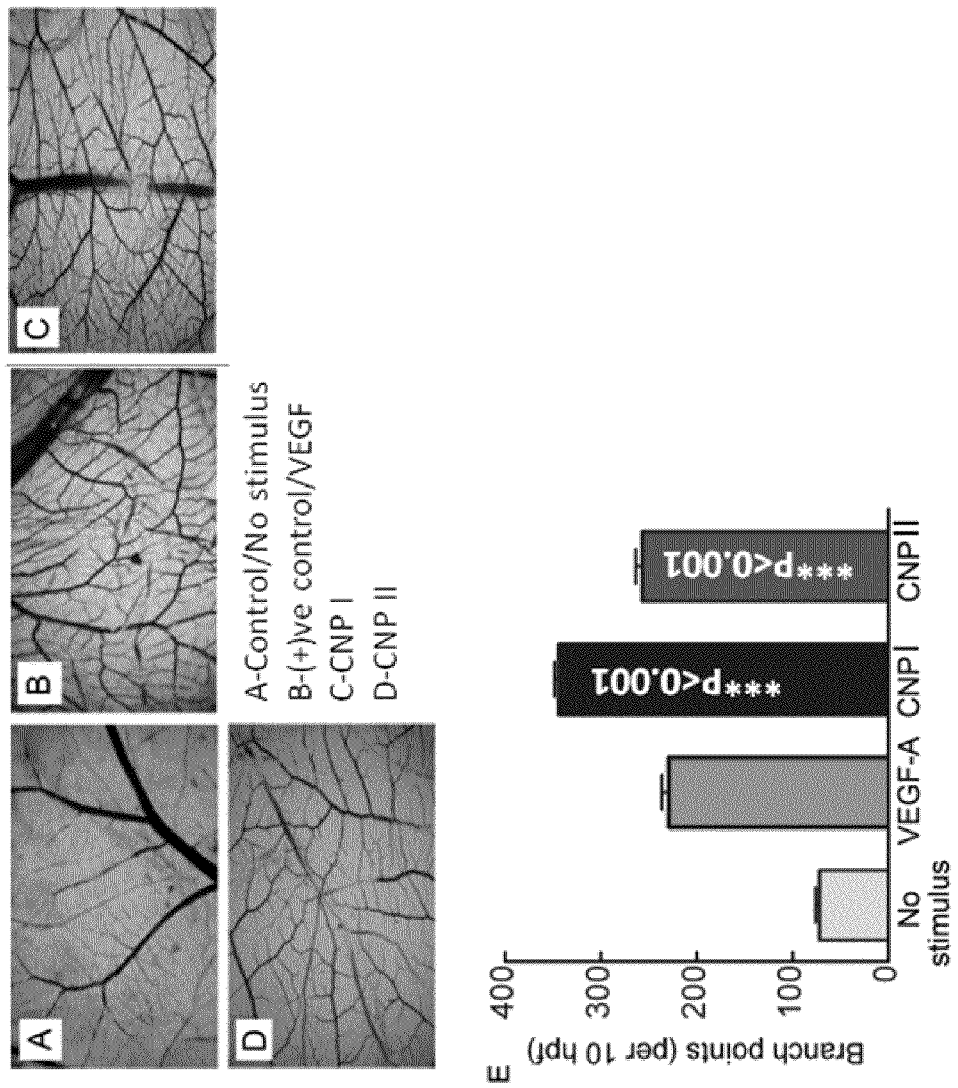
FIGS. 6A-D show CNP induced angiogenesis measured by Chick CAM assay. The extent of angiogenesis on CAM's treated with either (A) methylcellulose, (B) 50 ng of VEGF-A, (C) 1 μg of CNP1 or (D) 1 μg of CNP2. (E) The extent of CAM angiogenesis measured by counting the number of vascular sprouts from tertiary vessels in a minimum of 8 separate experiments. Hpf means high power field.

To support our observations using tube assays, we performed chick CAM sprouting assays. FIG. 6A-D represent the CAM after treatment with vehicle (A), VEGF (positive control) (B), 1 µM CNP-I (C) or 1 µM CNP-II (D). No vascular sprouting was observed when CAMs were treated with water only (control). Vascular sprouting was observed with CAMs, treated with VEGF (50 ng), as expected. The CAMs treated with CNP-I and CNP-II remarkably showed significant vascular sprouting. CNP-I promoted angiogenesis ($P \leq 0.001$) with matured vascular sprouting. CNP-II ($P \leq 0.001$) also presented similar angiogenesis but was slightly less robust compared to CNP-I. Quantitative data from the CAM assay is shown in FIG. 6E and reveals that CNP-I induces a 400% increase in angiogenesis compared to the un-stimulated control. Our results clearly demonstrate that CNPs induce endothelial cell proliferation as well as vascular sprouting.

Example 4

Cerium Oxide Nanoparticles Promote Angiogenesis Through a VEGF Regulated Pathway, by Regulating the Intracellular Oxygen Environment, and by Promoting Expression of HIF1α

This example shows that cerium oxide nanoparticles promote angiogenesis through a VEGF regulated pathway, by regulating the intracellular oxygen environment, and by stimulating the expression of HIF1α.

Figure 7:
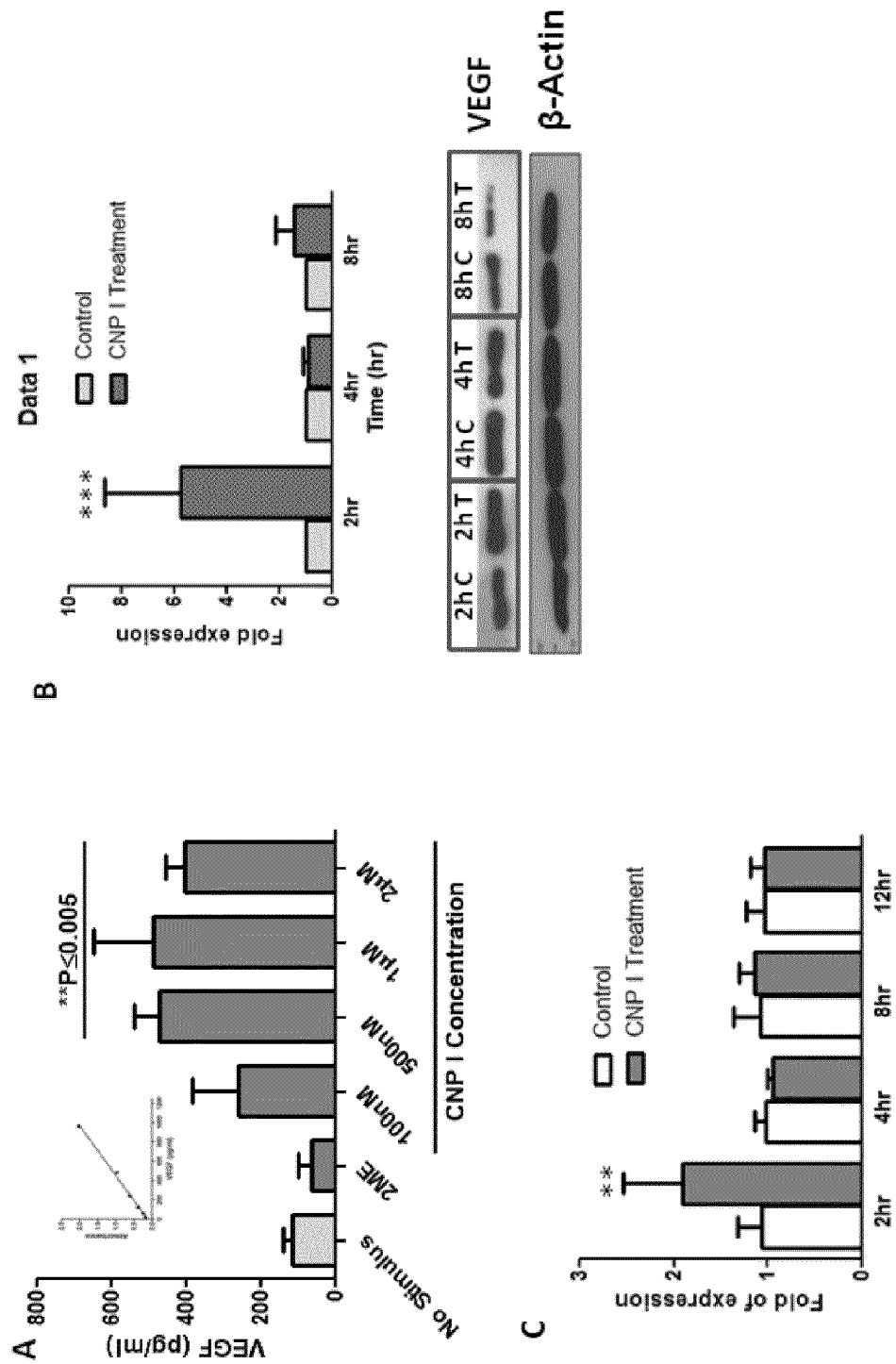
FIGS. 7A-C show that CNPs induced VEGF expression. (A) The amount of VEGF released from HUVEC cells to culture supernatant (exposed to varying concentrations of CNP-I) were measured by using ELISA. (B) The intracellular VEGF levels from HUVEC cells after CNP-I treatment (for different time points) was analyzed using the western blot technique. Semi-quantitative data obtained by densitometric analysis of western blot images are presented as mean±standard deviation from multiple experiments. (C) Changes in HUVEC cell m-RNA level after CNPI treatment were determined by RT-PCR.

Next, we analyzed VEGF expression in a culture medium of HUVEC cells by ELISA (FIG. 7A). Specifically, we focused on HUVECs exposed to CNP-I to further understand the molecular mechanism underpinning the angiogenic properties of the CNPs. A significant increase in VEGF levels in the culture medium for CNP-I treated cells was observed. The amount of VEGF reached a maximum when the cells were exposed to a concentration of 1 µM CNP-I. In comparison, the amount of excreted VEGF was less when a 2 µM CNP concentration was used. This suggests that a CNP concentration of about 1 µM the optimum or, at least, close to the optimum concentration of CNPs for stimulating angiogenesis induction.

The intracellular VEGF expression in CNP treated cells was estimated using western blotting as well as the RT-PCR technique. VEGF expression was estimated in the whole cell lysate, as a function of time, at a concentration of 1 µM (FIG. 7B). Densitometric analysis of western blot images, normalized to β-actin, showed almost three fold increase after a 2 hr treatment. Similar observations were observed in mRNA expression of VEGF, assayed by quantitative RT-PCR (FIG. 7C). From the ELISA, Western blotting and RT-PCR data it was clear that exposure of cells to CNPs induces pro-angiogenesis via a VEGF-dependent pathway.

Figure 8:
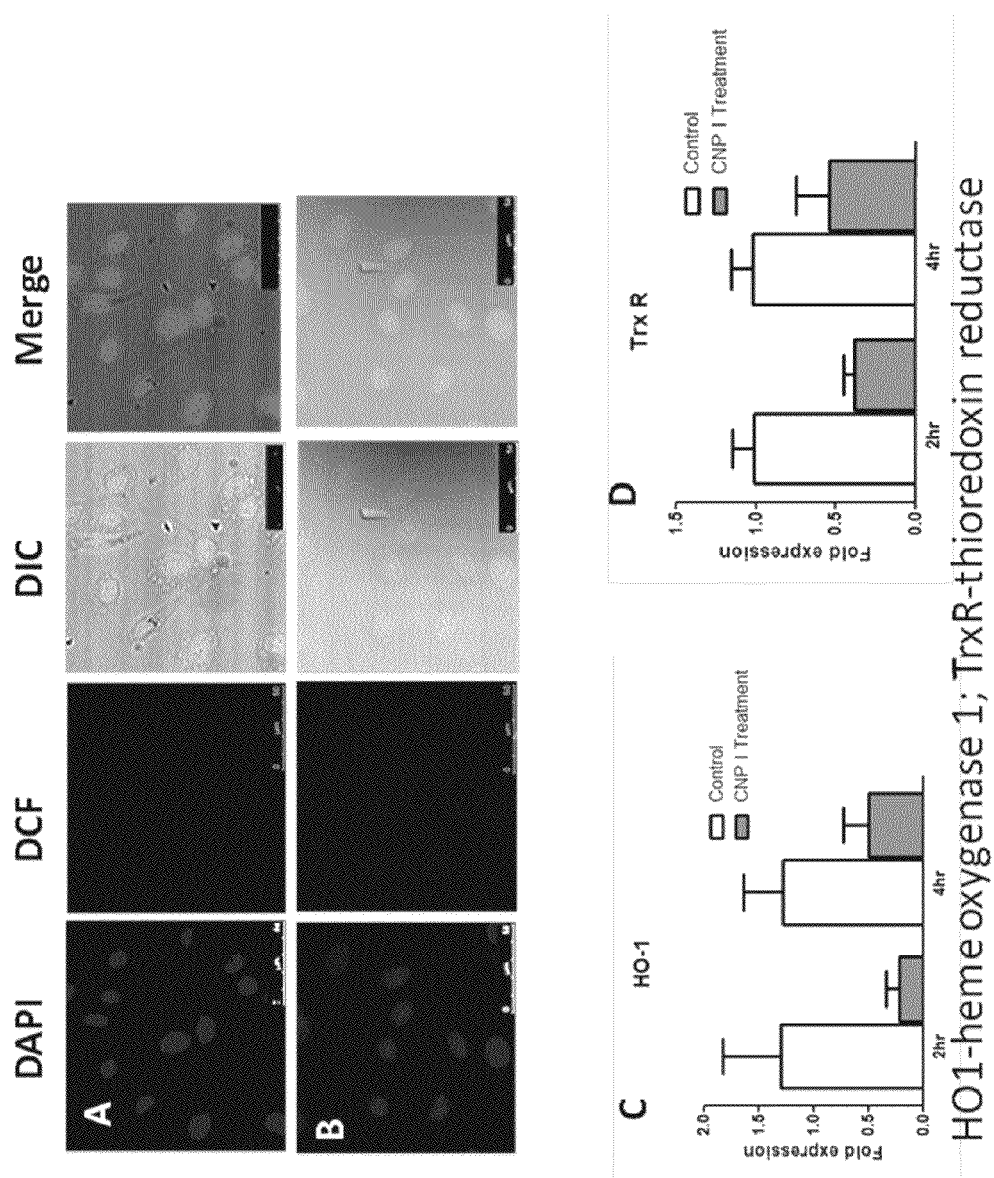
FIGS. 8A-D show that reactive oxygen species are not generated in HUVECs during CNP-I exposure. $DCFH_2$-DA (green, used for estimate ROS)/DAPI (blue, used for nuclear staining) staining were used. A, B, C and D are control, positive control, 30 ng VEGF and CNP-I respectively. Time dependent expression levels of two markers of cellular oxidative stress, hemeoxygenase 1 (E) and thioredoxin reductase (F) with or without CNP-I are shown.

Angiogenesis can be induced either by inducing low levels of intracellular reactive oxygen species (ROS) or by controlling the intracellular oxygen concentration to the cells. To identify the pathways by which CNPs induce the angiogenesis, we have analyzed intracellular ROS levels using 2',7'-dichlorodihydrofluorescein diacetate (DCF) (FIG. 8). No increase in ROS generation was observed in CNP-I treated cells (green-DCF positive) after 2 hr of CNP-I treatment. To further confirm, we analyzed the mRNA expression of hemeoxygenase-1 (HO1) and thioredoxin reductase (TrxR1), which is upregulated during oxidative stress. No increase in HO-1 or TrxR1 expression was observed up to 4 hr after addition of CNPs (FIG. 8C). These results indicate that exposure to CNPs most likely does not induce the angiogenesis by triggering higher levels of ROS, unlike $Eu(OH)_3$ nanorods which have been shown to induce angiogenesis through ROS generation.

Figure 9:
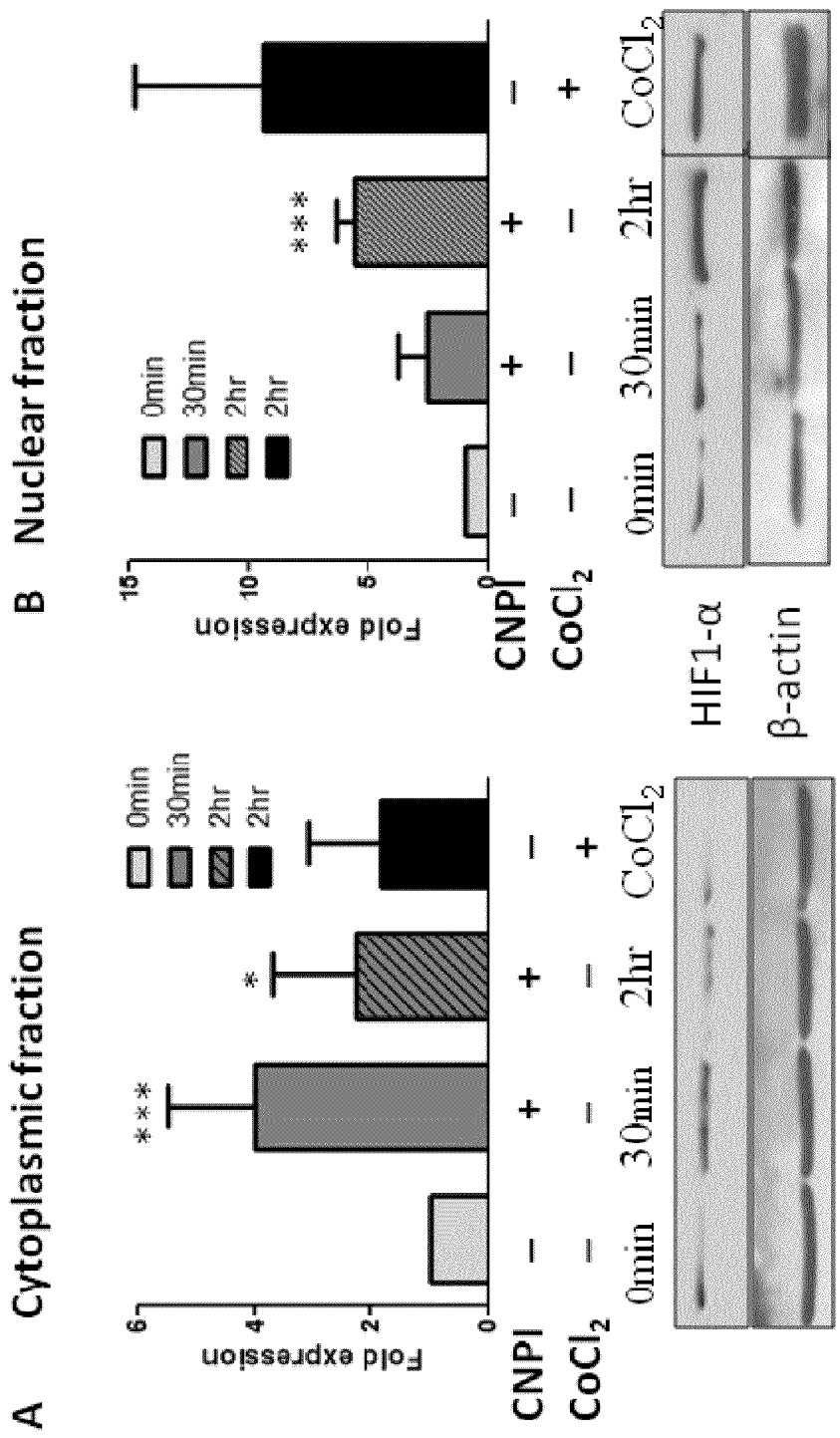
FIGS. 9A-D show that CNPs regulate of HIF1α by altering the intracellular oxygen concentration. Analysis of HIF1α in cytoplasmic (A) and nuclear (B) fractions at different time points (0 min, 30 min and 2 hr) in cells treated with 1 μM CNP-I or $CoCl_2$ used as a positive control (2 hr). Semi-quantitative data obtained by densitometric analysis are presented as mean±standard deviations from two independent experiments. The bar diagram is the fold of HIF1α amount as normalized to the β-actin expression. C shows the immunofluorescence image (left to right: Blue-DCF, Green-pimonidazole staining and merge image) of control and CNP treated HUVEC cells for different time durations (0 min, 30 min, 2 hr). The semi-quantitative data (D) calculated by measuring the fluorescence intensity of cells and presented as mean±standard deviations.
Figure 9:
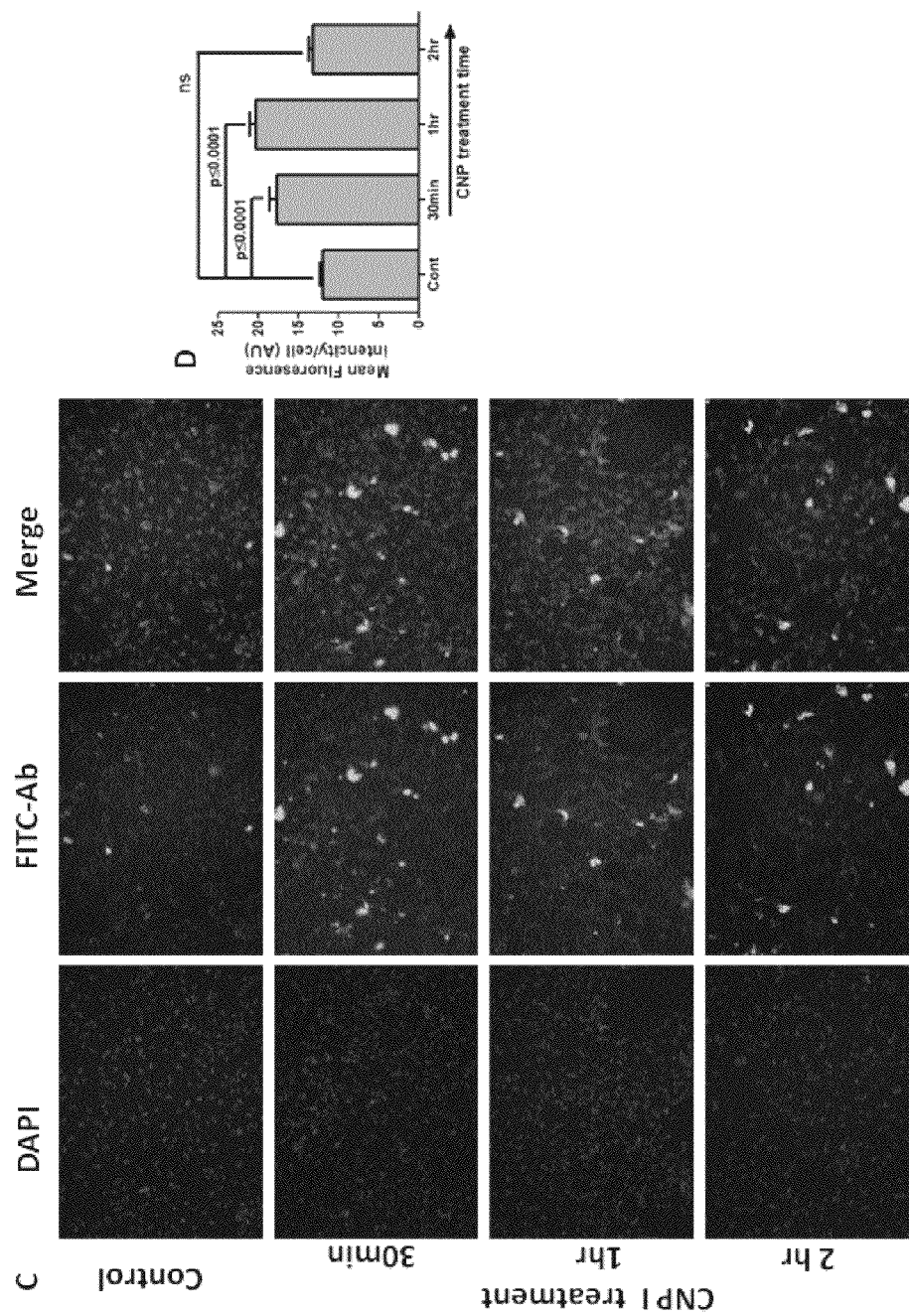
Figure 10:
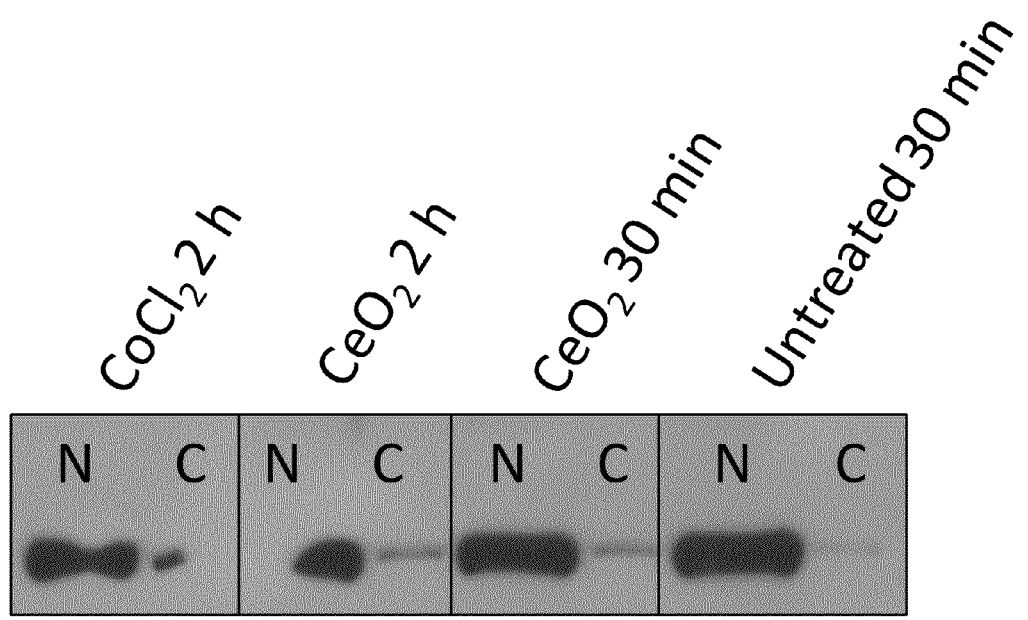
FIG. 10 shows immunoblot detection of HDAC-1 in nuclear and cytoplasmic extracts from HUVEC cells. HUVEC cells were treated with $CoCl_2$ (2 h) or 1000 nM CNPs for two different time durations (30 min and 2 hr). Nuclear and cytoplasmic lysates were prepared from treated and untreated cells and analyzed for enrichment of the nuclear marker protein HDAC-1. In all cases, nuclear extracts show an enhancement of nuclear proteins. Here, N=nuclear lysate and C=cytoplasmic lysate.

Angiogenesis can be regulated by the local oxygen concentration of the tissue. This pathway is indirectly governed by HIF1α regulation and transcriptional activation of angiogenic factors, which regulates gene expression involved in angiogenesis. We estimated the amount of HIF1α in the cytoplasm and the amount translocated into the nucleus of HUVECs following CNPI treatment. FIGS. 9A and B present the amount of HIF1α in cytoplasmic and nuclear fraction in control, CNP-I and $CoCl_2$ (Positive control) treated cells (30). A higher amount of HIF1α in cytoplasmic fraction was observed in cells treated with CNP-I (both 30 min and 2 hr treatment) (FIG. 9A). As expected, HIF1α nuclear translocation was also found to be increased in CNP-I treated cells (FIG. 9B). FIG. 10 shows the immunoblotting of nuclear marker histone deacetylase (HDAC-1), which confirmed successful separation of nuclear and cytoplasmic fraction of CNPI treated cells. HIF1α stabilization and translocation to the nucleus indicates that CNPs induced angiogenesis by regulating HIF1α.

Conventional immunostaining with pimonidazole was used to determine the intracellular $O_2$ level. Immunostaining images representing the intracellular $O_2$ level at different times (30 min, 1 hr and 2 hr) after CNP-I treatment are shown in FIG. 9C. FIG. 9D shows quantitative immunofluorescence data, which is proportional to the amount of $O_2$. Interestingly, low $O_2$ levels were observed immediately after CNP-I treatment up to 1 hr, however $O_2$ levels returned to normal after 2 hr of CNP-I treatment. This supports our hypothesis that CNPs activate HIF1α by modulation intracellular $O_2$ level.

Experimental Techniques

Cell Cultures.

HUVEC cells were obtained from Lonza Walkersville, Inc (Walkersville, Md., USA). HUVEC calls were grown in Endothelial Basal Media-2 (Lonza Walkersville) containing 2% FBS. Cultures were maintained at 37° C. and 5% $CO_2$ in humidified incubator and only passages 3-6 were used for experiments.

Cell Viability Assay.

The proliferation of HUVEC were assayed by colorimetric assay using MTT (3-(4,5 dimethylthiazol-2-yl)-2,5-diphenyl tetrazolium bromide) dye. Cells were cultured in 96-well plate at a density of $3 \times 10^3$ cells/well. Then cells were treated with different concentration of CNPs incubated for 24 hr and hr. MTT were added to the cell at a final concentration of 1.2 mM and incubated for 4 hr. Cells were lysed and insoluble formazan product was dissolved using buffer (10% SDS, 0.1 M HCl) and the absorbance 570 nm of each well were measured using SpectraMax 190 spectrophometer (Molecular Devices, Sunnyvale, Calif., USA). Cell proliferation was calculated by absorbing the CNPs treated samples/untreated control in percentage.

Endothelial Tube Formation Assay.

Growth factor reduced BD matrigel (BD Bioscience) was coated on a 96 well plate. $8.0-10.0 \times 10^3$ endothelial (HUVEC)

cells (passage 4-5) were plated per well. Cells were then treated with different concentrations of CNPs (10 nm to 10 µM). A positive control containing 30 ng/ml of rVEGF was used and a negative control was included the inhibitor 2-Methoxyestradiol. The number of tubes formed were calculated after 5 hr hours using brightfield microscopy and experiments were included triplicate cultures and carried out three times to determine reproducibility.

CAM Assay.

The CAM assay was performed as described by Vlahakis et al in *Journal of Biological Chemistry*, 282(20, pgs. 15187-15196 (2007) and by Fang et al in *Proceedings of the National Academy of Sciences*, 97(8), pgs. 3884-3889 (2000). The portions of these two articles that describe how a CAM assay is performed are incorporated herein by reference. Chicken eggs were purchased from Charles River Laboratories, Franklin, Conn. and maintained in a humidified 39° C. incubator (Lyon Electric, Chula Vista, Calif.). Pellets containing 0.5% methylcellulose plus recombinant human VEGF-A (50 ng), CNP1 (1 µg) or CNP2 (1 µg) were placed onto the CAM of 10-day-old chick embryo. Eggs were subsequently incubated at 39° C. and on Day 13 the CAM's were fixed and excised and then imaged using a digital camera (Canon PowerShot 6) attached to a stereomicroscope (Zeiss, Germany). Angiogenesis was quantified by counting the branch points arising from tertiary vessels from a minimum of 8 specimens from the three separate experiments.

DCFDHA Staining.

2500 cells/cover slip were seeded on a glass cover slip in a 6-well cell culture plate and allowed cells to adhere for 24 hrs. The next day, old media was replaced with fresh media containing CNPs, positive and negative control. Cells were then treated with 20 µM DCFDA and incubated for 30 min and washed with PBS. After washing cells were fixed under chilled methanol (−20° C.) for 8 min. Cells were again washed twice with PBS followed by incubation with DAPI for 8 min. Finally cells were washed and mounted in anti-fade mounting media (Calbiochem) and slides were prepared. These slides were stored at 4° C. until imaging under Leica TCS SP5 laser scanning confocal microscope with a 40× objective lens.

Pimonidazole Immunostaining.

Pimonidazole staining was carried out as described by Varia et al in *Gynecologic Oncology*, 71(2), pgs. 270-277 (1998). The portion of this article that describes how pimonidazole staining was performed is incorporated herein by reference. HUVEC cells were grown on a cover slip overnight and then treated with 1 µM CNP-I for 0 min (control), 30 min, 1 hr, and 2 hr. Then pimonidazole (final concentration 200 µM) was added to the cells and incubated for 45 min and cells were permeabilized/fixed with ice cold methanol for 10 min at room temperature and washed thoroughly with saline. Fixed cells were then blocked using 3% BSA in saline. Then cells were stained with FITC-conjugated monoclonal Hypoxyprobe-1 monoclonal antibody 1 (mAb1) (1:100 in 3% BSA) for one hr at room temperature and DAPI were used to stained the nucleus. Finally, cells were washed and mounted in anti-fade mounting media (Calbiochem) and examined under Fluorescence microscope. Using Image J 1.44p software (Wayne Rasband, National Institute of Health, USA) fluorescence intensity of 20 individual cells/field and different fields were estimated for each group and plotted as mean and standard deviation.

Western Blotting.

HUVEC cells were seeded on 60 mm petri plates coated with growth factor reduced BD matrigel (BD biosciences). Following CNPs treatment at 0.5 hr, 2 hr and 4 hr or $CoCl_2$ (positive control) cells were recovered by BD cell recovery kit. NE_PER Nuclear and Cytoplasmic Extraction Kit (Thermo) were used to isolate nuclear and cytoplasmic extract. Proteins were measured using Bradford assay. An equal amount of protein (25 ug) was fractionated by 4-20% SDS-PAGE gradient gels and transferred to PVDF membrane. 1:2000 diluted monoclonal anti-human VEGF and HIF1α antibody were used as primary antibody, incubated for overnight at 4° C. Anti-mouse IgG conjugated with HRP (1:15,000) used as 2ndary antibody, incubated for 1 hr at room temperature. A chemiluminescence method was adopted for developing the blot. Equal loading was ensured by re-probing of the blot using anti-β-actin antibody (1:1000). Densitometry analysis (ImageJ Software) was also carried out from the image to have semi quantitative data of HIF1α nuclear translocation.

ELISA Assay for VEGF.

Growth factor reduced BD matrigel (BD Bioscience) was coated on a 96 well plate. $8.0-10.0 \times 10^3$ endothelial (HUVEC) cells (passage 4-5) were plated per well as describe in endothelial tube formation assay. Then cells were treated with different concentration of CNPs and culture media were collected after 8 hr of incubation with nanoparticles. Amount of VEGF in culture media were assayed using an ELISA kit from Bio Scientific Corporation following the manufacturer's instructions.

RT-PCR.

Up-regulation or down-regulation of gene expressions flowing CNP treatment, if any, related to the angiogenesis were analyzed using RTPCR as a function of treatment time like 0 hr, 1 hr, 2 hr and 4 hr. Briefly, the total RNA were extracted similar as described in the previous section of PCR array. Equal quantity of mRNA (0.5 µg) were used for cDNA synthesis using Iscript cDNA synthesis kit (Bio-Rad). Oligonucleotides were designed using Primer3 Software available at www.simgene.com. RTPCR was carried out using Bio-Rad ICycler (Biomolecular Science Center) using SYBER green dye and the fold up-regulation or down-regulation of each gene were calculated from $C_T$ values using GAPDH as an internal standard. The oligonucleotides used are listed in Table 1.

TABLE 1

Human Real-Time PCR Primers, listed 5' to 3'

| | SEQ ID NO: | Sequence |
|---|---|---|
| HO-1 forward | SEQ ID NO: 1 | ctgagttcatgaggaactttcagaag |
| HO-1 reverse | SEQ ID NO: 2 | tggtacagggaggccatcac |
| Trx forward | SEQ ID NO: 3 | gcagatcgagagcaagactg |
| Trx reverse | SEQ ID NO: 4 | ctccagaaaattcacccacc |
| VEGF forward | SEQ ID NO: 5 | acacattgttggaagaagcagccc |
| VEGF reverse | SEQ ID NO: 6 | aggaaggtcaaccactcacacaca |
| GAPGH forward | SEQ ID NO: 7 | agtagaggcagggatgatgtt |
| GAPDH reverse | SEQ ID NO: 8 | ctttggtatcgtggaaggactc |

The invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

The invention claimed is:

1. A method of promoting angiogenesis in animal tissue, the method comprising contacting the tissue with a composition comprising cerium oxide nanoparticles effective for stimulating proliferation of endothelial cells associated with the tissue;
    wherein the cerium oxide nanoparticles are spherical with a diameter of about 3 nm to about 5 nm; and
    wherein the cerium oxide nanoparticles have a surface and a concentration of Ce(3+) greater than a concentration of Ce(4+) at the surface.

2. The method of claim 1, wherein the concentration of cerium oxide nanoparticles in the composition is between about 0.5 µM to about 1.5 µM.

3. The method of claim 1, wherein the concentration of cerium oxide nanoparticles in the composition is about 1 µM.

4. A method of promoting angiogenesis, the method comprising administering cerium oxide nanoparticles to a patient having a physiological condition that can be remediated by increasing endothelial cell proliferation;
    wherein the cerium oxide nanoparticles are spherical with a diameter of about 3 nm to about 5 nm; and
    wherein the cerium oxide nanoparticles have a surface and a concentration of Ce(3+) greater than a concentration of Ce(4+) at the surface.

5. The method of claim 4, wherein the cerium nanoparticles are provided in a composition at a concentration of between about 0.5 µM to about 1.5 µM.

6. The method of claim 5, wherein a concentration of cerium oxide nanoparticles in the composition is about 1 µM.

7. A method of promoting angiogenesis in a patient having a condition that can be remediated by increasing endothelial cell proliferation, the method comprising contacting a tissue of the patient with cerium oxide nanoparticles in an amount sufficient to transiently lower an intracellular oxygen concentration of the tissue, wherein the transient lowering the intracellular oxygen concentration stimulates expression of HIF1α, promotes proliferation of endothelial cells, and promotes angiogenesis in the tissue;
    wherein the cerium oxide nanoparticles are spherical with a diameter of about 3 nm to about 5 nm; and
    wherein the cerium oxide nanoparticles have a surface and a concentration of Ce(3+) greater than a concentration of Ce(4+) at the surface.

8. The method of claim 7, wherein the cerium nanoparticles are provided in a composition at a concentration of between about 0.5 µM to about 1.5 µM.

9. The method of claim 8, wherein the concentration of cerium oxide nanoparticles in the composition is about 1 µM.

* * * * *